US010222599B2

(12) United States Patent
Ouchi et al.

(10) Patent No.: US 10,222,599 B2
(45) Date of Patent: Mar. 5, 2019

(54) STRUCTURED ILLUMINATING APPARATUS, STRUCTURED ILLUMINATING MICROSCOPY APPARATUS, AND STRUCTURED ILLUMINATING METHOD

(71) Applicant: NIKON CORPORATION, Tokyo (JP)

(72) Inventors: Yumiko Ouchi, Yokohama (JP);
Kazuhiro Takasago, Yokohama (JP);
Hiroaki Nakayama, Kawasaki (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 14/327,189

(22) Filed: Jul. 9, 2014

(65) Prior Publication Data

US 2014/0320957 A1 Oct. 30, 2014

Related U.S. Application Data

(63) Continuation of application No. PCT/JP2013/000207, filed on Jan. 17, 2013.

(30) Foreign Application Priority Data

Jan. 18, 2012 (JP) .................................. 2012-008100
Oct. 29, 2012 (JP) .................................. 2012-238077

(51) Int. Cl.
*G02B 21/06* (2006.01)
*G02B 21/00* (2006.01)
(Continued)

(52) U.S. Cl.
CPC ........... *G02B 21/06* (2013.01); *G01N 21/648* (2013.01); *G01N 21/6458* (2013.01);
(Continued)

(58) Field of Classification Search
CPC ............ G02B 21/0076; G02B 21/0044; G02B 21/0064; G02B 21/0032; G02B 21/06;
(Continued)

(56) References Cited

U.S. PATENT DOCUMENTS 6,239,909 B1    5/2001   Hayashi et al.
6,864,960 B2 *  3/2005   Koehler .............. G03F 7/70183
                                                              355/53
(Continued)

FOREIGN PATENT DOCUMENTS

DE      101 55 002 A1    5/2003
EP       1 617 259 A1    1/2006
(Continued)

OTHER PUBLICATIONS

International Search Report issued in International Application No. PCT/JP2013/000207 dated Mar. 19, 2013.
(Continued)

*Primary Examiner* — Nicholas R. Pasko
(74) *Attorney, Agent, or Firm* — Oliff PLC

(57) ABSTRACT

A structured illuminating apparatus includes a branching unit branching an exit light flux from a light source into at least two branched light fluxes, an illuminating optical system making the two branched light fluxes to be respectively collected at mutually different positions on a pupil plane of an objective lens and making the two branched light fluxes to be interfered with each other to illuminate a specimen with an interference fringe of the two branched light fluxes, and an adjusting unit adjusting a height from an optical axis of the illuminating optical system to two collecting points formed on the pupil plane of the objective lens by the two branched light fluxes.

28 Claims, 16 Drawing Sheets

(51) Int. Cl.
  *G02B 21/36* (2006.01)
  *G02B 27/58* (2006.01)
  *G01N 21/64* (2006.01)
(52) U.S. Cl.
  CPC ..... *G02B 21/0032* (2013.01); *G02B 21/0076* (2013.01); *G02B 21/367* (2013.01); *G02B 27/58* (2013.01)
(58) Field of Classification Search
  CPC ............... G02B 26/08; G02B 26/0808; G02B 26/0816; G02B 26/0875; G02B 26/0883; G02B 26/0891; G01N 21/6458; G01N 21/648
  USPC ............ 359/358–398, 558, 566, 568, 577
  See application file for complete search history.

(56) References Cited

U.S. PATENT DOCUMENTS

| | | | | |
|---|---|---|---|---|
| 7,283,209 | B2 * | 10/2007 | Brotsack | G03F 7/70108 355/53 |
| 7,369,305 | B2 * | 5/2008 | Wolleschensky | G02B 15/173 359/380 |
| 7,848,017 | B2 * | 12/2010 | Ouchi | G02B 21/14 359/384 |
| 8,115,806 | B2 | 2/2012 | Osawa et al. | |
| 8,289,622 | B2 * | 10/2012 | Loriette | G02B 21/0032 359/370 |
| 2005/0281516 | A1 * | 12/2005 | Okazaki | G02B 6/4206 385/96 |
| 2006/0012875 | A1 | 1/2006 | Wolleschensky | |
| 2007/0076293 | A1 | 4/2007 | Wolleschensky et al. | |
| 2008/0158668 | A1 * | 7/2008 | Ouchi | G02B 5/1871 359/385 |
| 2009/0109417 | A1 * | 4/2009 | Tanitsu | G02B 27/0927 355/67 |
| 2009/0168158 | A1 * | 7/2009 | Schwertner | G02B 21/0024 359/385 |
| 2009/0250632 | A1 * | 10/2009 | Kempe | G01N 21/6458 250/459.1 |
| 2010/0141750 | A1 * | 6/2010 | Osawa | G02B 21/06 348/79 |
| 2012/0026311 | A1 * | 2/2012 | Ouchi | G02B 21/06 348/79 |
| 2012/0140057 | A1 * | 6/2012 | Borck | G01N 21/6458 348/79 |
| 2013/0229665 | A1 * | 9/2013 | Nomura | G02B 21/06 356/601 |
| 2013/0302905 | A1 * | 11/2013 | Kalkbrenner | G01N 21/6428 436/172 |
| 2015/0185463 | A1 * | 7/2015 | Ohki | G02B 21/06 348/79 |

FOREIGN PATENT DOCUMENTS

| | | |
|---|---|---|
| EP | 1 617 271 A2 | 1/2006 |
| EP | 1 617 271 A3 | 5/2006 |
| JP | A-2006-268004 | 10/2006 |
| JP | 2007-199571 A | 8/2007 |
| JP | A-2009-63666 | 3/2009 |
| JP | A-2009-98215 | 5/2009 |
| WO | WO 2007/043382 A1 | 4/2007 |
| WO | WO 2011018181 A1 * | 2/2011 ......... G01N 21/6458 |
| WO | WO-2011018181 A1 * | 2/2011 ......... G01N 21/6458 |
| WO | WO 2011/135819 A1 | 11/2011 |
| WO | 2014/017067 A1 | 1/2014 |

OTHER PUBLICATIONS

Aug. 21, 2015 Extended Search Report issued in British Patent Application No. 13739110.8.
Jun. 2, 2015 Office Action issued in Japanese Patent Application No. 2013-554252.
International Preliminary Report on Patentability issued in International Application No. PCT/JP2013/000207 dated Jul. 22, 2014.

* cited by examiner

US 10,222,599 B2

STRUCTURED ILLUMINATING APPARATUS, STRUCTURED ILLUMINATING MICROSCOPY APPARATUS, AND STRUCTURED ILLUMINATING METHOD

CROSS-REFERENCE TO RELATED APPLICATIONS

This application is a continuation application of International Application PCT/JP2013/000207, filed Jan. 17, 2013, designating the U.S., and claims the benefit of priority from Japanese Patent Application Nos. 2012-008100 and 2012-238077, filed on Jan. 18, 2012 and Oct. 29, 2012, respectively, the entire contents of which are incorporated herein by reference.

BACKGROUND

1. Field

The present application relates to a structured illuminating apparatus, a structured illuminating microscopy apparatus, and a structured illuminating method.

2. Description of the Related Art

In a field of observation and measurement of sample (specimen), in order to achieve a resolution exceeding a performance of an objective lens, there has been proposed a structured illuminating microscopy which illuminates a specimen with a spatially-modulated illuminating light (structured illuminating light) to obtain an image (modulated image), and removes a modulation component included in the modulated image (performs demodulation), to thereby generate a super-resolved image (demodulated image) of the specimen (refer to Specification of U.S. Pat. No. 6,239,909, for example).

Particularly, in a structured illuminating microscopy disclosed in Specification of U.S. Pat. No. 6,239,909, a light flux exited from a light source is branched into a plurality of light fluxes by a diffraction grating or the like, and the light fluxes are made to be interfered with each other in the vicinity of a specimen to form an interference fringe, and the interference fringe is used as the structured illuminating light.

However, although a demand for switching a light source wavelength may arise also in the structured illuminating microscopy, similar to another microscopy, it was proved that a super-resolution effect (a ratio of a resolving power achieved by modulation to a resolving power achieved by non-modulation) varies, if the light source wavelength is switched.

The present application has been made in view of such circumstances, and a proposition thereof is to provide a structured illuminating apparatus, a structured illuminating microscopy apparatus, and a structured illuminating method capable of adjusting or controlling a super-resolution effect.

SUMMARY

An example of a structured illuminating apparatus of the present embodiment includes a branching unit branching an exit light flux from a light source into at least two branched light fluxes, an illuminating optical system making the two branched light fluxes to be respectively collected at mutually different positions on a pupil plane of an objective lens and making the two branched light fluxes to be interfered with each other to illuminate a specimen with interference fringes of the two branched light fluxes, and an adjusting unit adjusting a height from an optical axis of the illuminating optical system to two collecting points formed on the pupil plane of the objective lens by the two branched light fluxes.

Further, an example of a structured illuminating microscopy apparatus of the present embodiment includes the structured illuminating apparatus of the present embodiment and an image-forming optical system forming an image on a light detector by an observational light flux from the specimen modulated by the interference fringe.

DETAILED DESCRIPTION OF THE EMBODIMENTS

First Embodiment

Hereinafter, a structured illuminating microscopy apparatus will be described as a first embodiment of the present invention.

Figure 1:
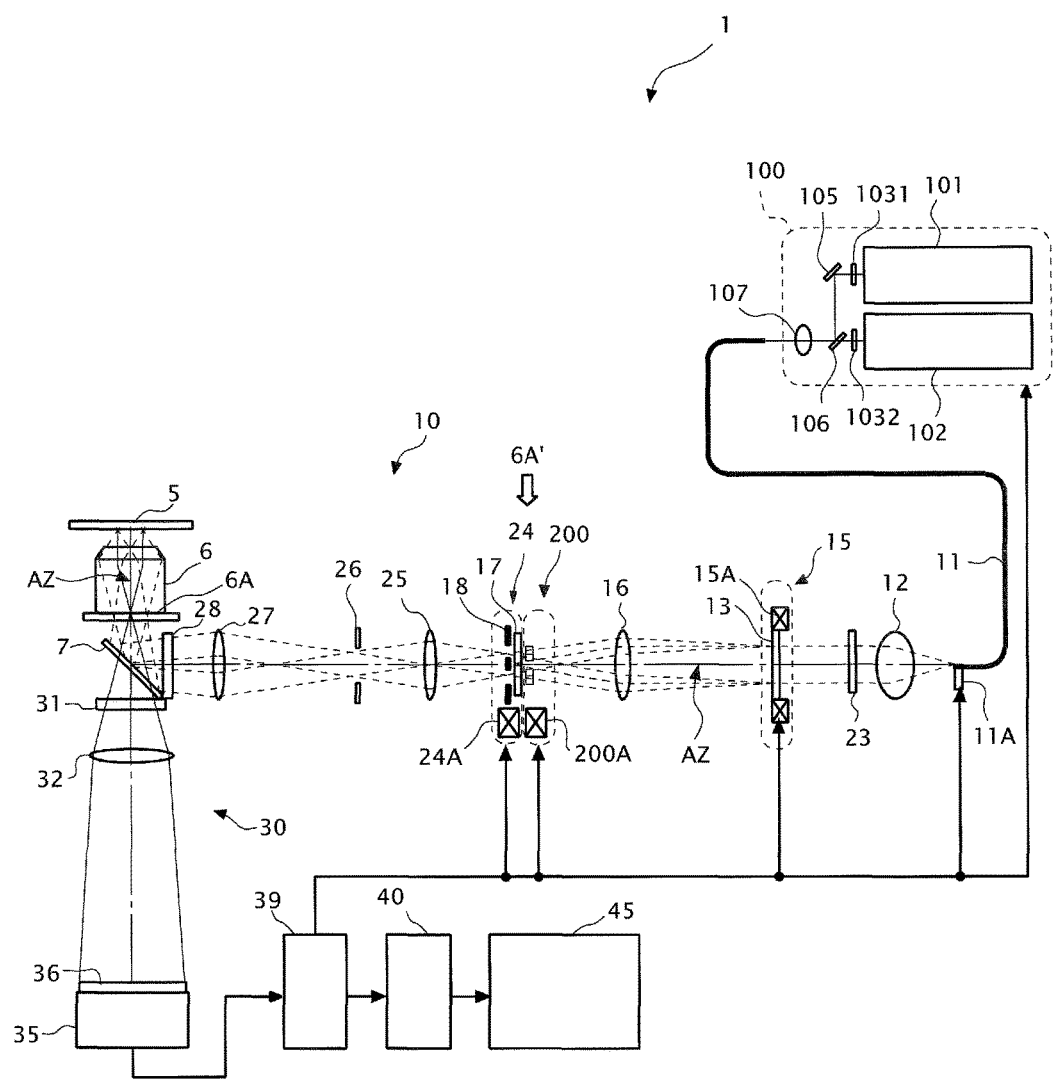
FIG. 1 is a configuration diagram of a structured illuminating microscopy apparatus 1 of a first embodiment.

FIG. 1 is a configuration diagram of a structured illuminating microscopy apparatus 1. Here, a case where the structured illuminating microscopy apparatus 1 is used as a total internal reflection fluorescence microscopy (TIRFM) which observes an extremely thin layer on a surface of a sample (specimen) 5 having a fluorescence, will be described.

First, a configuration of the structured illuminating microscopy apparatus 1 will be described.

As illustrated in FIG. 1, there are provided, in the structured illuminating microscopy apparatus 1, a laser unit 100, an optical fiber 11, an illuminating optical system 10, an image-forming optical system 30, an imaging sensor 35, a controlling device 39, an image storing-calculating device 40, and an image displaying device 45. Note that the illuminating optical system 10 is one of epi-illumination type, and illuminates the specimen 5 by utilizing an objective lens 6 and a dichroic mirror 7 which are parts of the image-forming optical system 30.

In the laser unit 100, there are provided a first laser light source 101, a second laser light source 102, shutters 1031 and 1032, a mirror 105, a dichroic mirror 106, and a lens 107. Each of the first laser light source 101 and the second laser light source 102 is a coherent light source, and exit wavelengths of the laser light sources are mutually different. Here, it is assumed that a wavelength $\lambda 1$ of the first laser light source 101 is longer than a wavelength $\lambda 2$ of the second laser light source 102 ($\lambda 1 > \lambda 2$). The first laser light source 101, the second laser light source 102, and the shutters 1031 and 1032 are respectively driven by the controlling device 39.

The optical fiber 11 is formed of, for example, a polarization-maintaining single-mode fiber to guide a laser light exited from the laser unit 100. A position in an optical axis AZ direction of an exit end of the optical fiber 11 can be adjusted by a position adjusting mechanism 11A. The position adjusting mechanism 11A is driven by the controlling device 39.

In the illuminating optical system 10, there are disposed a collector lens 12, a polarizing plate 23, a beam branching part 15, a collecting lens 16, a space adjusting part 200, a beam selecting part 24, a lens 25, a field stop 26, a field lens 27, an excitation filter 28, the dichroic mirror 7, and the objective lens 6, in this order from an exit end side of the optical fiber 11.

The beam branching part 15 is provided with a diffractive optical element (diffraction grating) 13 and a translatory shifting mechanism 15A, the space adjusting part 200 is provided with a plurality of prisms (details will be described later) and an adjusting mechanism 200A, and the beam selecting part 24 is provided with a ½ wavelength plate 17, a beam selecting element 18, and a rotating mechanism 24A. Note that the translatory shifting mechanism 15A, the adjusting mechanism 200A, and the rotating mechanism 24A are driven by the controlling device 39.

In the image-forming optical system 30, there are disposed the objective lens 6, the dichroic mirror 7, a barrier filter 31, and a secondary objective lens 32, in this order from a side of the specimen 5.

The specimen 5 is, for example, a culture fluid dropped on a surface of parallel-plate glass, and a cell having a fluorescence (a cell stained by a fluorescent dye) exists in the vicinity of a glass interface in the culture fluid. Both of a first fluorescent area which is excited by a light with the wavelength $\lambda 1$ and a second fluorescent area which is excited by a light with the wavelength $\lambda 2$ are exhibited in the cell.

The objective lens 6 is configured as an objective lens of immersion type (oil-immersion type) so as to enable a total internal reflection fluorescence observation. Specifically, a gap between the objective lens 6 and the glass of the specimen 5 is filled with immersion liquid (oil).

The imaging sensor 35 is a two-dimensional imaging sensor formed of a CCD, a CMOS or the like. When the imaging sensor 35 is driven by the controlling device 39, it captures an image formed on its imaging plane 36, and generates an image. The image is taken into the image storing-calculating device 40 via the controlling device 39.

The controlling device 39 drives and controls the laser unit 100, the position adjusting mechanism 11A, the translatory shifting mechanism 15A, the adjusting mechanism 200A, the rotating mechanism 24A, and the imaging sensor 35.

The image storing-calculating device 40 performs calculation with respect to the image given via the controlling device 39, stores the calculated image in a not-illustrated internal memory, and sends at the same time the image to the image displaying device 45.

Next, a behavior of laser light in the structured illuminating microscopy apparatus 1 will be described.

A laser light with the wavelength $\lambda 1$ exited from the first laser light source 101 (first laser light) is incident on the mirror 105 via the shutter 1031, and reflected by the mirror 105 to be incident on the dichroic mirror 106. Meanwhile, a laser light with the wavelength $\lambda 2$ exited from the second laser light source 102 (second laser light) is incident on the dichroic mirror 106 via the shutter 1032, and combined with the first laser light. The first laser light and the second laser light exited from the dichroic mirror 106 are incident on an incident end of the optical fiber 11 via the lens 107.

Note that the controlling device 39 can switch the wavelength (=light source wavelength) of laser light incident on the incident end of the optical fiber 11 between the long wavelength $\lambda 1$ and the short wavelength $\lambda 2$ by controlling the shutters 1031 and 1032 of the laser unit 100.

The laser light incident on the incident end of the optical fiber 11 propagates in the optical fiber 11, and generates a point light source at the exit end of the optical fiber 11. The laser light exited from the point light source is converted into a collimated light flux by the collector lens 12 to be incident on the diffraction grating 13 via the polarizing plate 23, and then branched into diffracted light fluxes with respective orders. The diffracted light fluxes with respective orders are collected by the collecting lens 16 at mutually different positions on a pupil conjugate plane 6A'.

Here, the pupil conjugate plane 6A' indicates a focal position of the collecting lens 16 (rear focal position), and a position conjugated with a pupil 6A of the later-described objective lens 6 (a position at which ± first-order diffracted lights are collected) via the field lens 27 and the lens 25. Note that it is set that a position determined by a person skilled in the art by taking the design requirements such as aberration, vignetting and the like of the objective lens 6, the field lens 27, and the lens 25 into consideration, also falls into the concept of "conjugate position" mentioned here).

Further, since the laser light exited from the optical fiber 11 is basically linearly polarized, the polarizing plate 23 can be omitted, but, the polarizing plate 23 is effective to securely cut an excess polarization component. Further, in order to increase a utilization efficiency of the laser light, an axis of the polarizing plate 23 desirably coincides with a polarization direction of the laser light exited from the optical fiber 11.

The diffracted light fluxes with respective orders directed to the pupil conjugate plane 6A' are incident on the beam selecting part 24 disposed in the vicinity of the pupil conjugate plane 6A' via the space adjusting part 200 similarly disposed in the vicinity of the pupil conjugate plane 6A'.

Here, the structured illuminating microscopy apparatus 1 of the present embodiment is used as the TIRFM (total internal reflection fluorescence microscopy), so that the beam selecting part 24 makes only a pair of diffracted light fluxes (only ± first-order diffracted light fluxes, in this case) to be selectively passed therethrough out of the incident diffracted light fluxes with respective orders.

The ± first-order diffracted light fluxes passed through the beam selecting part 24 are converted into convergent lights by the field lens 27 after forming a conjugated plane of the diffraction grating 13 in the vicinity of the field stop 26 via the lens 25, are reflected by the dichroic mirror 7 after passing through the excitation filter 28, and are collected at mutually different positions on the pupil plane 6A of the objective lens 6.

The respective ± first-order diffracted light fluxes collected on the pupil plane 6A are turned into collimated light fluxes when being exited from a tip of the objective lens 6, and interfere with each other on a surface of the specimen 5, to thereby form an interference fringe. The interference fringe is used as structured illuminating light.

Here, since the structured illuminating microscopy apparatus 1 of the present embodiment is used as the TIRFM (total internal reflection fluorescence microscopy), an incident angle of each of the ± first-order diffracted light fluxes incident on the surface of the specimen 5 satisfies a generation condition of evanescent field (total internal reflection condition). Hereinafter, the total internal reflection condition is referred to as "TIRF-condition".

In order to satisfy the TIRF-condition, collecting points of the ± first-order diffracted light fluxes on the pupil plane 6A are required to be positioned within a predetermined ring-belt-shaped area at an outmost circumference of the pupil plane 6A. The above-described space adjusting part 200 is provided to adjust a space between collecting points of a pair of diffracted light fluxes on the pupil plane 6A, and to set the collecting points of the both diffracted light fluxes to be positioned within the predetermined ring-belt-shaped area (details will be described later). As a result of the adjustment, an evanescent field formed by an interference fringe is generated in the vicinity of the surface of the specimen 5.

When the specimen 5 is illuminated by such interference fringe, a moiré fringe corresponding to a difference between a pitch structure of the interference fringe and a pitch structure of a fluorescent area on the specimen 5 appears, in which on the moiré fringe, a structure of high frequency of the fluorescent area is shifted to a side of frequency that is lower than the original frequency, so that a fluorescence that exhibits this structure is directed to the objective lens 6 at an angle smaller than the original angle. Therefore, when the specimen 5 is illuminated by the interference fringe, even structural information of the high frequency of the fluorescent area is transmitted by the objective lens 6.

The fluorescence generated in the vicinity of the surface of the specimen 5 (evanescent field) is incident on the objective lens 6, and converted into a collimated light by the objective lens 6, and after that, the collimated light transmits through the dichroic mirror 7 and the barrier filter 31, and forms a modulated image of the specimen 5 on the imaging plane 36 of the imaging sensor 35 via the secondary objective lens 32.

This modulated image is subjected to imaging by the imaging sensor 35, resulting in that a modulated image of the fluorescent area is generated. The modulated image is taken into the image storing-calculating device 40 via the controlling device 39. Further, the image storing-calculating device 40 performs publicly-known demodulating calculation on the modulated image taken therein, thereby generating a demodulated image (super-resolved image). Further, the super-resolved image is stored in the internal memory (not illustrated) of the image storing-calculating device 40, and at the same time, it is sent to the image displaying device 45. Note that as the publicly-known demodulating calculation, a method disclosed in specification of U.S. Pat. No. 8,115,806 is employed, for example.

Next, the diffraction grating 13 will be described in detail.

Figure 2A:
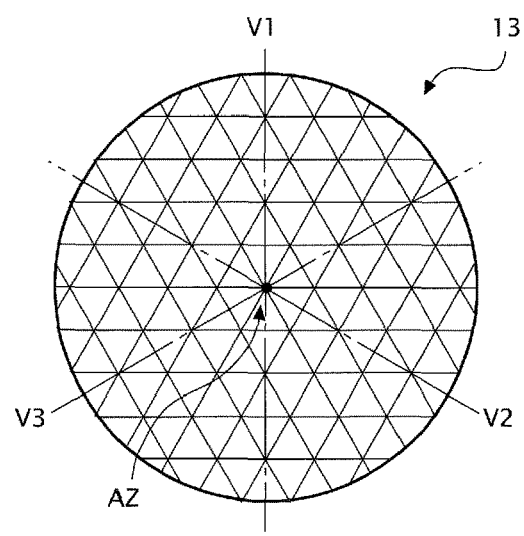
FIGS. 2A and 2B are diagrams explaining a diffraction grating 13.
Figure 2B:
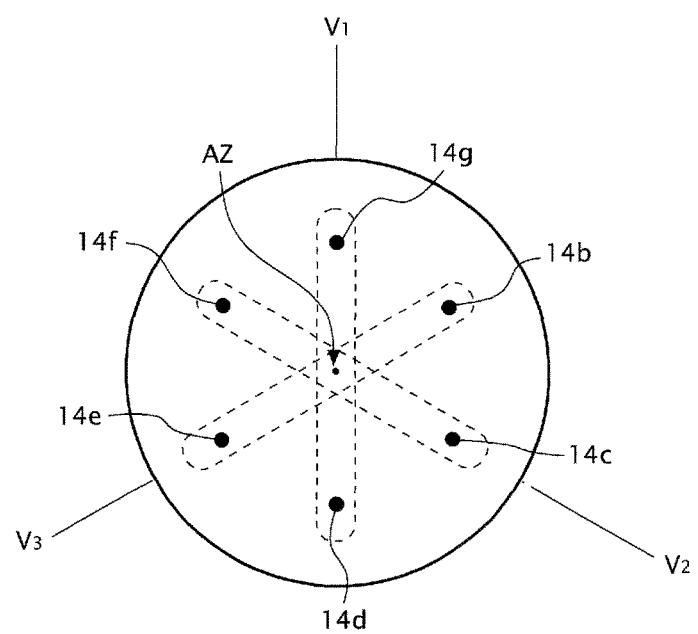

FIG. 2A is a diagram in which the diffraction grating 13 is seen from the optical axis AZ direction, and FIG. 2B is a diagram illustrating a positional relationship of collecting points formed on a pupil conjugate plane by ± first-order diffracted light fluxes. Note that FIG. 2A is a schematic diagram, so that a structural pitch of the diffraction grating 13 illustrated in FIG. 2A is not always the same as an actual structural pitch.

As illustrated in FIG. 2A, the diffraction grating 13 is a diffraction grating having pitch structures along mutually different plural directions, in a plane perpendicular to the optical axis AZ of the illuminating optical system 10. A material of the diffraction grating 13 is a glass, for example. Here, the diffraction grating 13 is a three-direction diffraction grating having a pitch structure along each of a first direction $V_1$, a second direction $V_2$, and a third direction $V_3$, the directions being different from one another by 120°, and it is assumed that pitches of the pitch structures are common.

Note that the pitch structure of the diffraction grating 13 may be either a pitch structure of density type formed by utilizing a density (transmittance) or a pitch structure of phase type formed by utilizing a level difference (phase difference), but the pitch structure of phase type is more preferable in a point that a diffraction efficiency of + first-order diffracted light is high.

A collimated light flux incident on such a diffraction grating 13 is converted into a first diffracted light flux group branched along the first direction $V_1$, a second diffracted light flux group branched along the second direction $V_2$, and a third diffracted light flux group branched along the third direction $V_3$.

The first diffracted light flux group includes a 0th-order diffracted light flux and ± first-order diffracted light fluxes, and the ± first-order diffracted light fluxes each having a common order, out of the above, propagate in directions symmetric about the optical axis AZ.

In like manner, the second diffracted light flux group includes a 0th-order diffracted light flux and ± first-order diffracted light fluxes, and the ± first-order diffracted light fluxes each having a common order, out of the above, propagate in directions symmetric about the optical axis AZ.

In like manner, the third diffracted light flux group includes a 0th-order diffracted light flux and ± first-order diffracted light fluxes, and the ± first-order diffracted light fluxes each having a common order, out of the above, propagate in directions symmetric about the optical axis AZ.

The ± first-order diffracted light fluxes of the first diffracted light flux group, the ± first-order diffracted light fluxes of the second diffracted light flux group, and the ± first-order diffracted light fluxes of the third diffracted light flux group, are collected, by the aforementioned collecting lens 16, at mutually different positions within the pupil conjugate plane.

Further, as illustrated in FIG. 2B, collecting points 14d and 14g of the ± first-order diffracted light fluxes of the first diffracted light flux group are symmetric about the optical axis AZ, and an arranging direction of the collecting points 14d and 14g corresponds to the first direction $V_1$.

If a wavelength of laser light exited from the optical fiber 11 is set to λ, a pitch of the diffraction grating 13 is set to P, and a focal length of the lens 16 is set to fc, a distance D from the optical axis AZ to each of the collecting points 14d and 14g is represented by the following expression.

$$D = 2fc\lambda/P$$

Therefore, when the wavelength of the laser light is changed, the collecting points 14d and 14g are displaced.

Further, collecting points 14c and 14f of the ± first-order diffracted light fluxes of the second diffracted light flux group are symmetric about the optical axis AZ, and an arranging direction of the collecting points 14c and 14f corresponds to the second direction $V_2$. Note that a distance from each of the collecting points 14c and 14f of the second diffracted light flux group to the optical axis AZ is the same as the distance from each of the collecting points 14d and 14g of the first diffracted light flux group to the optical axis AZ.

Further, collecting points 14b and 14e of the ± first-order diffracted light fluxes of the third diffracted light flux group are symmetric about the optical axis AZ, and an arranging direction of the collecting points 14b and 14e corresponds to the third direction $V_3$. Note that a distance from each of the collecting points 14b and 14e of the third diffracted light flux group to the optical axis AZ is the same as the distance from each of the collecting points 14d and 14g of the first diffracted light flux group to the optical axis AZ.

Note that the "collecting point" described here indicates a barycenter position of an area having an intensity of 80% or more of a maximum intensity. For this reason, the illuminating optical system 10 does not have to collect a light flux up to when a perfect collecting point is formed.

Further, the diffraction grating 13 described above can be translatory shifted by the translatory shifting mechanism 15A (refer to FIG. 1) formed of a piezoelectric motor or the like. A direction in which the diffraction grating 13 is translatory shifted by the translatory shifting mechanism 15A is a direction perpendicular to the optical axis AZ of the illuminating optical system 10, and a direction which is not perpendicular to each of the above-described first direction $V_1$, second direction $V_2$, and third direction $V_3$. When the diffraction grating 13 is translatory shifted in this direction, a phase of an interference fringe is shifted (details will be described later).

Next, functions of the ½ wavelength plate 17 and the beam selecting element 18 will be described in detail.

Figure 3A:
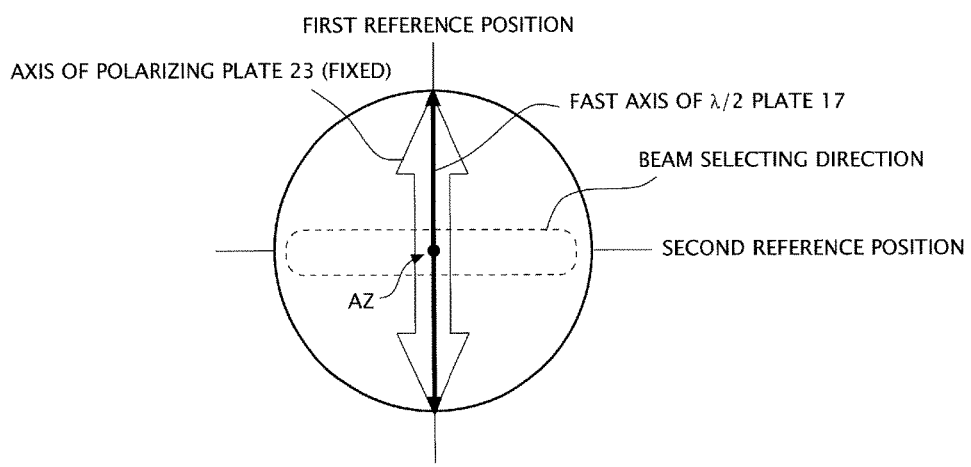
FIGS. 3A and 3B are diagrams explaining a function of a ½ wavelength plate 17.
Figure 3B:
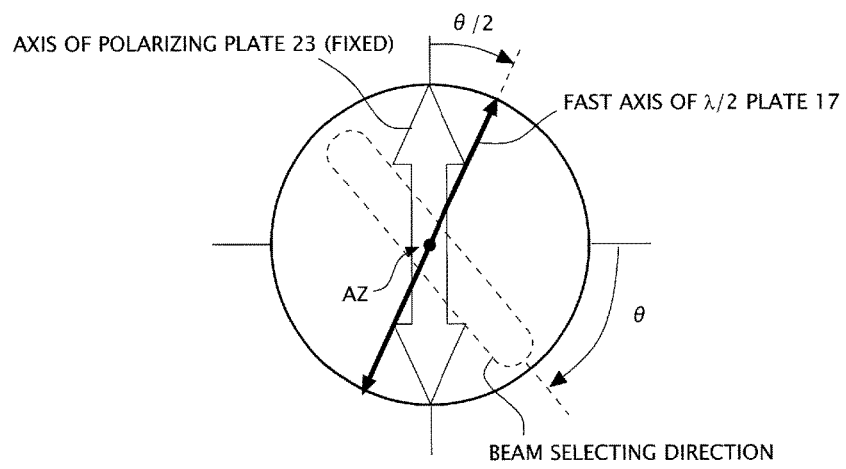
Figure 4A:
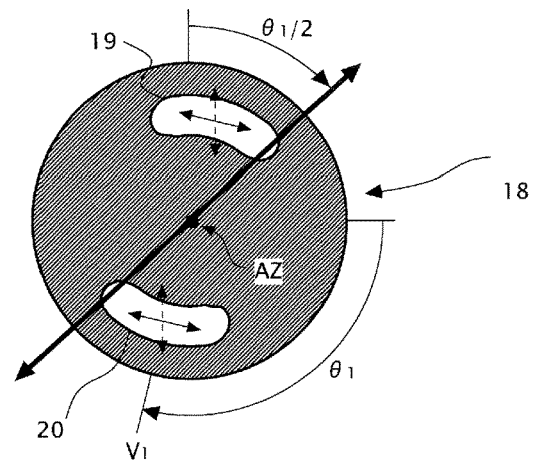
FIGS. 4A, 4B, and 4C are diagrams explaining a function of a beam selecting element 18.
Figure 4B:
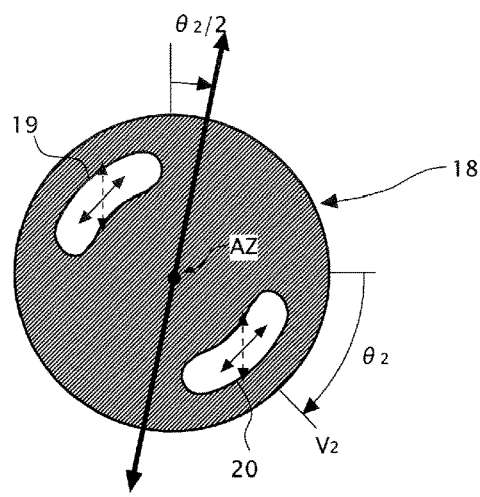
Figure 4C:
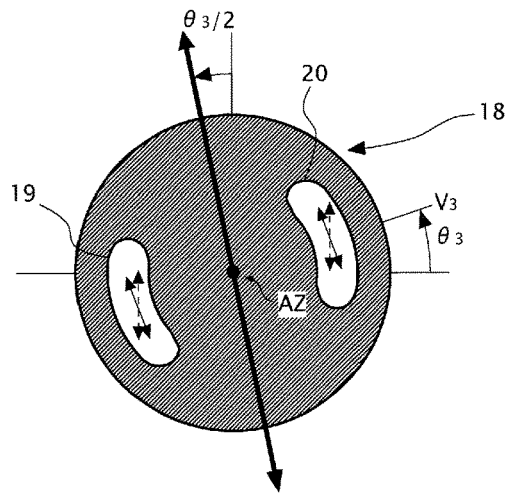

FIGS. 3A and 3B are diagrams explaining the function of the ½ wavelength plate 17, and FIGS. 4A, 4B, and 4C are diagrams explaining the function of the beam selecting element 18.

The ½ wavelength plate 17 is a wavelength plate which sets a polarization direction of incident diffracted light fluxes of respective orders, as illustrated in FIGS. 3A and 3B, and the beam selecting element 18 is a mask which makes only the ± first-order diffracted light fluxes of any one of the first to third diffracted light flux groups to be selectively passed therethrough, as illustrated in FIGS. 4A, 4B, and 4C.

Further, the ½ wavelength plate 17 and the beam selecting element 18 can be rotated around the optical axis AZ by the rotating mechanism 24A (refer to FIG. 1). The rotating mechanism 24A switches the ± first-order diffracted light fluxes to be selected among the first to third diffracted light flux groups by rotating the beam selecting element 18, and maintains a polarization direction when the selected ± first-order diffracted light fluxes are incident on the specimen 5 to S polarization, by rotating the ½ wavelength plate 17 around the optical axis AZ in conjunction with the beam selecting element 18.

Specifically, the ½ wavelength plate 17 and the beam selecting element 18 switch the direction of an interference fringe while keeping a state of the interference fringe. Hereinafter, conditions for keeping the state of fringe will be concretely described.

First, a direction of a fast axis of the ½ wavelength plate 17 is required to be set so that the branching direction of the ± first-order diffracted light fluxes to be selected (any one of the first direction $V_1$ to the third direction $V_3$) and a polarization direction of the ± first-order diffracted light fluxes become perpendicular to each other. Note that the fast axis of the ½ wavelength plate 17 described here indicates a direction in which a phase delay amount of a light polarized in a direction of the axis passes through the ½ wavelength plate 17 is minimized.

Further, an aperture pattern of the beam selecting element 18 is formed of a first aperture portion 19 and a second aperture portion 20 through which one and the other of the ± first-order diffracted light fluxes belonging to the same diffracted light flux group are individually passed, and a length of each of the first aperture portion 19 and the second aperture portion 20 around the optical axis AZ is set to a length which enables the diffracted light flux linearly polarized in the above-described direction to pass through each of the aperture portions. Therefore, a shape of each of the first aperture portion 19 and the second aperture portion 20 is a shape close to a partial ring-belt shape.

Here, as illustrated in FIG. 3A, a rotating position of the ½ wavelength plate 17 when the direction of the fast axis of the ½ wavelength plate 17 becomes parallel to a direction of axis of the polarizing plate 23, is set to a reference of the rotating position of the ½ wavelength plate 17 (referred to as "first reference position", hereinafter).

Further, a rotating position of the beam selecting element 18 when a beam selecting direction (=a branching direction of the ± first-order diffracted light fluxes to be selected) by the beam selecting element 18 becomes perpendicular to the direction of axis of the polarizing plate 23, is set to a reference of the rotating position of the beam selecting element 18 (referred to as "second reference position", hereinafter).

At this time, a rotation amount of the ½ wavelength plate 17 from the first reference position should be controlled to be half of a rotation amount of the beam selecting element 18 from the second reference position, as illustrated in FIG. 3B. Specifically, when the rotation amount of the ½ wavelength plate 17 from the first reference position is θ/2, the rotation amount of the beam selecting element 18 from the second reference position should be set to θ.

Accordingly, when the rotating mechanism 24A (refer to FIG. 1) rotates the beam selecting direction of the beam selecting element 18 in the right direction from the second reference position by a rotation angle $\theta_1$, as illustrated in FIG. 4A, to select the ± first-order diffracted light fluxes of the first diffracted light flux group (the branching direction is the first direction $V_1$), the rotating mechanism 24A rotates the direction of the fast axis of the ½ wavelength plate 17 in the right direction from the first reference position by a rotation angle $\theta_1/2$.

At this time, although the polarization directions of the diffracted light fluxes of respective orders before the diffracted light fluxes pass through the ½ wavelength plate 17 are parallel to the direction of axis of the polarizing plate 23, as indicated by dashed bidirectional arrows in FIG. 4A, the polarization directions of the diffracted light fluxes of respective orders after the diffracted light fluxes pass through the ½ wavelength plate 17 are rotated in the right direction by the rotation angle $\theta_1$, so that the polarization directions of the selected ± first-order diffracted light fluxes become perpendicular to the branching direction of the ± first-order diffracted light fluxes (the first direction $V_1$), as indicated by solid bidirectional arrows in FIG. 4A.

In other words, the direction of the fast axis of the ½ wavelength plate 17 is a direction in accordance with the branching direction of the ± first-order diffracted light fluxes selected by the beam selecting element 18 (=the first direction $V_1$), and is set to a direction of bisector of an angle made by the polarization direction originally possessed by each of the ± first-order diffracted light fluxes which are incident on the ½ wavelength plate 17 (=the axial direction of the polarizing plate 23) and the polarization direction which should be possessed by each of the ± first-order diffracted light fluxes which exit from the ½ wavelength plate 17 (=perpendicular to the first direction $V_1$).

Further, when the rotating mechanism 24A (refer to FIG. 1) rotates the beam selecting direction of the beam selecting element 18 in the right direction from the second reference position by a rotation angle $\theta_2$, as illustrated in FIG. 4B, to select the ± first-order diffracted light fluxes of the second diffracted light flux group (the branching direction is the second direction $V_2$), the rotating mechanism 24A rotates the direction of the fast axis of the ½ wavelength plate 17 in the right direction from the first reference position by a rotation angle $\theta_2/2$.

At this time, although the polarization directions of the diffracted light fluxes of respective orders before the diffracted light fluxes pass through the ½ wavelength plate 17 are parallel to the direction of axis of the polarizing plate 23, as indicated by dashed bidirectional arrows in FIG. 4B, the polarization directions of the diffracted light fluxes of respective orders after the diffracted light fluxes pass through the ½ wavelength plate 17 are rotated in the right direction by the rotation angle $\theta_2$, so that the polarization directions of the selected ± first-order diffracted light fluxes become perpendicular to the branching direction of the ± first-order diffracted light fluxes (the second direction $V_2$), as indicated by solid bidirectional arrows in FIG. 4B.

In other words, the direction of the fast axis of the ½ wavelength plate 17 is a direction in accordance with the branching direction of the ± first-order diffracted light fluxes selected by the beam selecting element 18 (=the second direction $V_2$), and is set to a direction of bisector of an angle made by the polarization direction originally possessed by each of the ± first-order diffracted light fluxes which are incident on the ½ wavelength plate 17 (=the axial direction of the polarizing plate 23) and the polarization direction which should be possessed by each of the ± first-order diffracted light fluxes which exit from the ½ wavelength plate 17 (=perpendicular to the second direction $V_2$).

Further, when the rotating mechanism 24A (refer to FIG. 1) rotates the beam selecting direction of the beam selecting element 18 in the left direction (when seen from the specimen side, which is similarly applied to the following description) from the second reference position by a rotation angle $\theta_3$, as illustrated in FIG. 4C, to select the ± first-order diffracted light fluxes of the third diffracted light flux group (the branching direction is the third direction $V_3$), the rotating mechanism 24A rotates the direction of the fast axis of the ½ wavelength plate 17 in the left direction from the first reference position by a rotation angle $\theta_3/2$.

At this time, although the polarization directions of the diffracted light fluxes of respective orders before the diffracted light fluxes pass through the ½ wavelength plate 17 are parallel to the direction of axis of the polarizing plate 23, as indicated by dashed bidirectional arrows in FIG. 4C, the polarization directions of the diffracted light fluxes of respective orders after the diffracted light fluxes pass through the ½ wavelength plate 17 are rotated in the left direction by the rotation angle $\theta_3$, so that the polarization directions of the selected ± first-order diffracted light fluxes become perpendicular to the branching direction of the ± first-order diffracted light fluxes (the third direction $V_3$), as indicated by solid bidirectional arrows in FIG. 4C.

In other words, the direction of the fast axis of the ½ wavelength plate 17 is a direction in accordance with the branching direction of the ± first-order diffracted light fluxes selected by the beam selecting element 18 (=the third direction $V_3$), and is set to a direction of bisector of an angle made by the polarization direction originally possessed by each of the ± first-order diffracted light fluxes which are incident on the ½ wavelength plate 17 (=the axial direction of the polarizing plate 23) and the polarization direction which should be possessed by each of the ± first-order diffracted light fluxes which exit from the ½ wavelength plate 17 (=perpendicular to the third direction $V_3$).

Therefore, the rotating mechanism 24A is only required to move the ½ wavelength plate 17 and the beam selecting element 18, in a conjunctive manner, at a gear ratio of 2:1.

Figure 5:
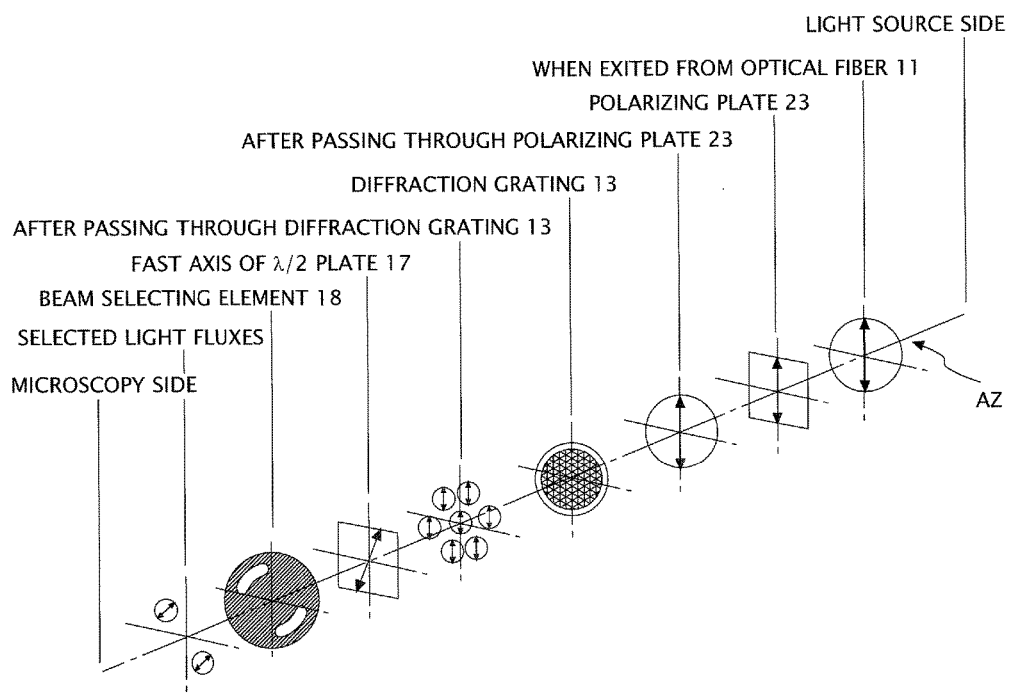
FIG. 5 is a diagram explaining the functions of the ½ wavelength plate 17 and the beam selecting element 18.

FIG. 5 is a diagram explaining the functions of the ½ wavelength plate 17 and the beam selecting element 18 described above. Note that in FIG. 5, bidirectional arrows surrounded by a circular frame indicate a polarization direction of a light flux, and bidirectional arrows surrounded by a quadrangular frame indicate an axial direction of the optical element.

Note that in the above-described explanation, the rotatable ½ wavelength plate 17 is used for keeping the ± first-order diffracted light fluxes which are incident on the specimen 5 to the S polarization, but, it is also possible to use, instead of the rotatable ½ wavelength plate 17, a liquid crystal element which is disposed in a fixed manner, and to make the liquid crystal element function as the ½ wavelength plate 17. If an orientation of the liquid crystal element is electrically controlled, a refractive index anisotropy of the liquid crystal element can be controlled, so that it is possible to rotate the fast axis as the ½ wavelength plate around the optical axis AZ. Incidentally, there is another method for keeping the ± first-order diffracted light fluxes which are incident on the specimen 5 to the S polarization (which will be described later).

Figure 6:
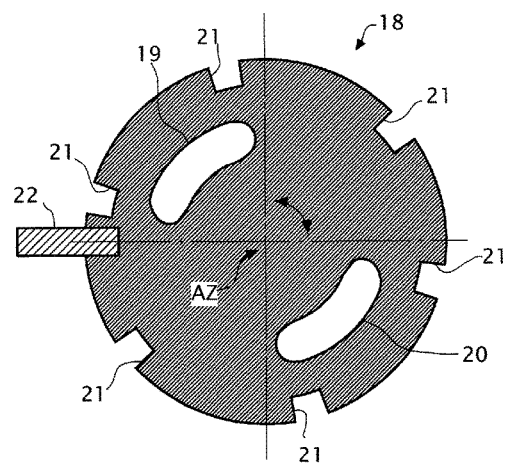
FIG. 6 is a diagram explaining a shape of the beam selecting element 18.

Further, as illustrated in FIG. 6, a plurality of (six, in an example illustrated in FIG. 6) cutouts 21 are formed on an outer peripheral portion of the beam selecting element 18, and the rotating mechanism 24A (refer to FIG. 1) is provided with a timing sensor 22 for detecting the cutouts 21. Accordingly, the rotating mechanism 24A can detect not only the rotating position of the beam selecting part 18 but also the rotating position of the ½ wavelength plate 17.

Next, a function of the translatory shifting mechanism 15A (refer to FIG. 1) will be described in detail.

Figure 7A:
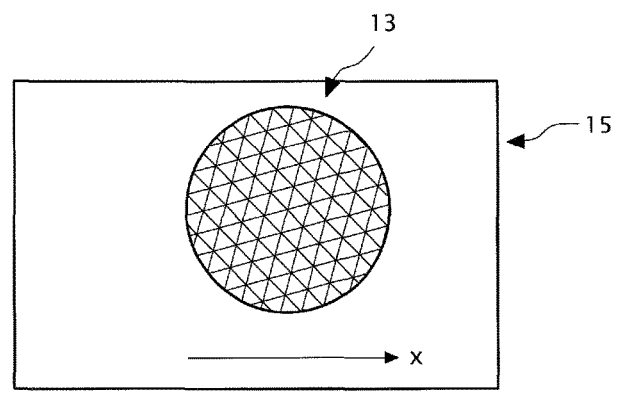
FIGS. 7A and 7B are diagrams explaining a function of a translatory shifting mechanism 15A.
Figure 7B:
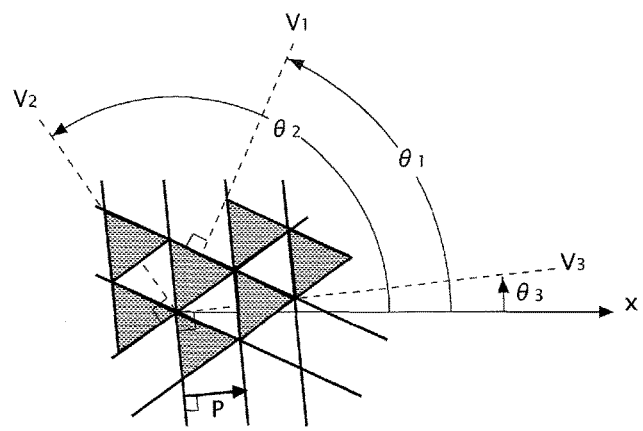

FIGS. 7A and 7B are diagrams explaining the function of the translatory shifting mechanism 15A.

First, in order to enable the aforementioned demodulating calculation, for example, three pieces or more of modulated images with different phases of an interference fringe are used where the images are modulated images related to the same specimen 5 and related to the interference fringe in the same direction. This is because a modulated image generated by the structured illuminating microscopy apparatus 1 includes a 0th-order modulation component, a + first-order modulation component, and a − first-order modulation component being information of structure in which a spatial frequency is modulated by the interference fringe, out of a structure of a fluorescent area of the specimen 5, and a plurality of pieces of modulated images are required to make the three unknown parameters to be known in the demodulating calculation.

Accordingly, in order to shift the phase of the interference fringe, the translatory shifting mechanism 15A shifts the diffraction grating 13 along a direction perpendicular to the optical axis AZ of the illuminating optical system 10 where the direction not perpendicular to all of the aforementioned first direction $V_1$, second direction $V_2$, and third direction $V_3$ (x direction) as illustrated in FIG. 7A.

However, a shift amount L of the diffraction grating 13 required to shift the phase of the interference fringe by a desired shift amount $\phi$ is not always the same when the beam selecting direction selected by the beam selecting part 24 is the first direction $V_1$, when the direction is the second direction $V_2$, and when the direction is the third direction $V_3$.

As illustrated in FIG. 7B, if a structural pitch (pitch) in each of the first direction $V_1$, the second direction $V_2$, and the third direction $V_3$ of the diffraction grating 13 is set to P, an angle made by a shift direction of the diffraction grating 13 (x direction) and the first direction $V_1$ is set to $\theta_1$, an angle made by the shift direction of the diffraction grating 13 (x direction) and the second direction $V_2$ is set to $\theta_2$, and an angle made by the shift direction of the diffraction grating 13 (x direction) and the third direction $V_3$ is set to $\theta_3$, a shift amount $L_1$ in the x direction of the diffraction grating 13 required when the beam selecting direction is the first direction $V_1$ is represented by $L_1=\phi \times P/(4\pi \times |\cos \theta_1|)$, a shift amount $L_2$ in the x direction of the diffraction grating 13 required when the beam selecting direction is the second direction $V_2$ is represented by $L_2=\phi \times P/(4\pi \times |\cos \theta_2|)$, and a shift amount $L_3$ in the x direction of the diffraction grating 13 required when the beam selecting direction is the third direction $V_3$ is represented by $L_3=\phi \times P/(4\pi \times |\cos \theta_3|)$.

Specifically, the shift amount L in the x direction of the diffraction grating 13 required to set the phase shift amount of the interference fringe to have the desired value $\phi$ is represented, as in an expression (1), by the angle $\theta$ made by the wavelength selecting direction (any one of the first direction $V_1$, the second direction $V_2$, and the third direction $V_3$) and the x direction.

$$L=\phi \times P/(4\pi \times |\cos \theta|) \qquad (1)$$

Incidentally, a shift amount L in the x direction of the diffraction grating 13 required to set a phase shift amount $\phi$ of fringe of the structured illuminating light to $2\pi$ is represented by $P/(2\times|\cos \theta|)$. This is an amount corresponding to a half pitch of the diffraction grating 13. Specifically, only by shifting the diffraction grating 13 by a half pitch, the phase of the structured illuminating light can be shifted by one pitch (this is because a fringe pitch of the structured illuminating light formed of the ± first-order diffracted lights corresponds to twice the structural pitch of the diffraction grating 13).

Next, the space adjusting part 200 will be described in detail.

Figure 8A:
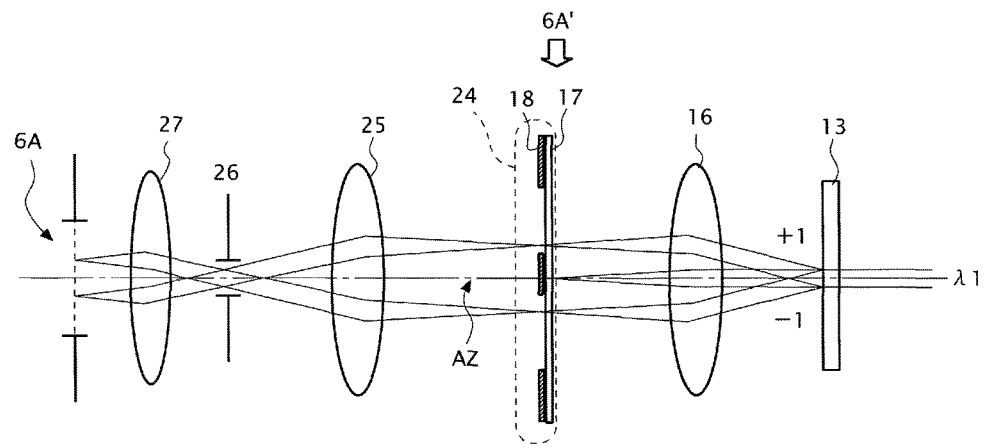
FIGS. 8A and 8B are diagrams illustrating optical paths of an illuminating optical system 10 which does not include a space adjusting part 200.
Figure 8B:
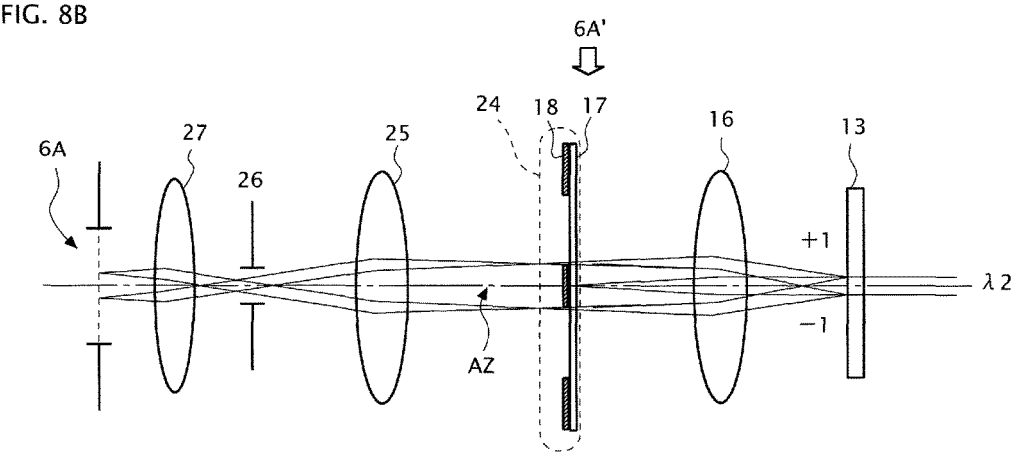
Figure 9A:
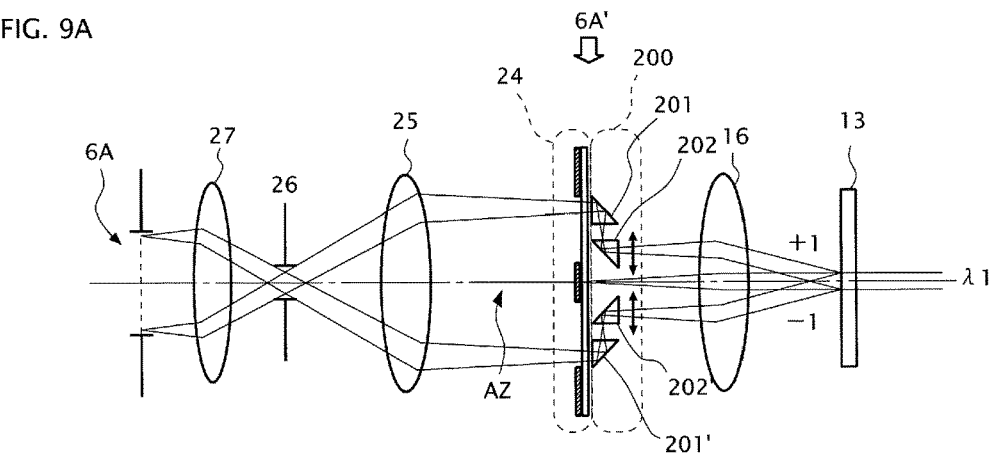
FIGS. 9A and 9B are diagrams illustrating optical paths of the illuminating optical system 10 which includes a space adjusting part 200 of the first embodiment.
Figure 9B:
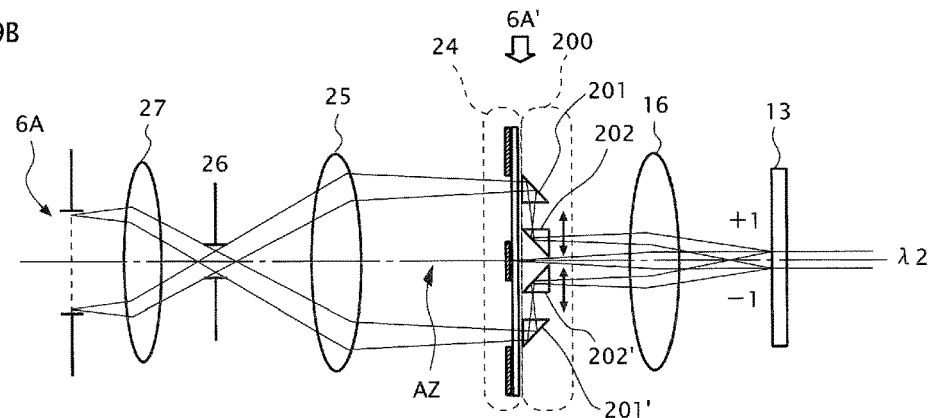

FIGS. 8A and 8B illustrate optical paths of the illuminating optical system 10 when the space adjusting part 200 is not provided, and FIGS. 9A and 9B illustrate optical paths of the illuminating optical system 10 when the space adjusting part 200 is provided. Each of FIG. 8A and FIG. 9A illustrates a case where a light source wavelength is a long wavelength $\lambda 1$, and each of FIG. 8B and FIG. 9B illustrates a case where the light source wavelength is a short wavelength $\lambda 2$. Note that an illustration of the excitation filter 28 and the dichroic mirror 7 is omitted in FIGS. 8A and 8B and FIGS. 9A and 9B.

As illustrated from FIGS. 8A to 8B, when the light source wavelength is switched from the long wavelength $\lambda 1$ to the short wavelength $\lambda 2$, a diffraction angle (branching amount) of the ± first-order diffracted light fluxes which exit from the diffraction grating 13 becomes small, so that if, tentatively, the space adjusting part 200 is not provided, a height of collecting point of each of the ± first-order diffracted light fluxes on the pupil plane 6A from the optical axis AZ is changed, as illustrated at the far left in FIGS. 8A and 8B. Note that here, a distance from the optical axis AZ to a light ray is simply referred to as "height".

If the height of the collecting point is changed between the wavelengths $\lambda 1$ and $\lambda 2$ as above, a super-resolution effect is changed between the wavelengths $\lambda 1$ and $\lambda 2$. The super-resolution effect is a ratio of a resolving power achieved by modulation (a resolving power achieved by the structured illuminating light) based on a resolving power achieved by non-modulation (a resolving power achieved by a uniform illuminating light), and (super-resolution effect)=(resolving power achieved by structured illuminating light)/(resolving power achieved by uniform illuminating light)=(pupil diameter+distance between collecting points)/(pupil diameter) is satisfied. Therefore, the larger the ratio of the height of the collecting point with respect to a pupil radius of the objective lens 6, the higher the super-resolution effect becomes.

Accordingly, as illustrated in FIGS. 9A and 9B, the space adjusting part 200 is provided with a prism 202 for deflecting a direction of an optical path of one of the ± first-order diffracted light fluxes (which is set to + first-order diffracted light flux, in this case) incident from a side of the collecting lens 16 (here, the direction deflected by the prism 202 is set to a direction separating from the optical axis AZ), and a prism 201 for reflecting the + first-order diffracted light flux deflected by the prism 202, and returning the direction of the optical path of the + first-order diffracted light flux to the original direction (direction same as that of the optical path when the light flux is incident on the prism 202).

Further, as illustrated in FIGS. 9A and 9B, the space adjusting part 200 is provided with a prism 202' for deflecting a direction of an optical path of the other of the ± first-order diffracted light fluxes (− first-order diffracted light flux, in this case) which is incident from the side of the collecting lens 16 (here, the direction deflected by the prism 202' is set to a direction separating from the optical axis AZ), and a prism 201' for reflecting the − first-order diffracted light flux deflected by the prism 202', and returning the direction of the optical path of the − first-order diffracted light flux to the original direction (direction same as that of the optical path when the light flux is incident on the prism 202').

Note that the diffracted light fluxes used for the structured illuminating light of the present embodiment are the diffracted light fluxes having a common order (± first-order diffracted light fluxes) as described above, and optical paths of the ± first-order diffracted light fluxes have to keep a relationship in which they are symmetric about the optical axis AZ.

Accordingly, a disposition relationship of reflecting surfaces of the prisms 202 and 202' on an upstream side of the space adjusting part 200 is kept to a relationship symmetric about the optical axis AZ, and a disposition relationship of reflecting surfaces of the prisms 201 and 201' on a downstream side of the space adjusting part 200 is kept to a relationship symmetric about the optical axis AZ.

Further, as illustrated from FIGS. 9A to 9B, the prisms 202 and 202' on the upstream side of the space adjusting part 200 can change a space therebetween while keeping the mutual positional relationship to a relationship symmetric about the optical axis AZ.

Therefore, as illustrated in FIGS. 9A and 9B, when the space between the prisms 202 and 202' is adjusted in accordance with the light source wavelength, a space between collecting points of the ± first-order diffracted light fluxes on the pupil plane 6A can be kept constant. Accordingly, the super-resolution effect is also kept constant.

Further, when the space adjusting part 200 is not provided as illustrated in FIGS. 8A and 8B, the collecting points of the ± first-order diffracted light fluxes on the pupil plane 6A are not always positioned within the predetermined ring-belt-shaped area (the TIRF area satisfying the generation condition of the evanescent field).

Accordingly, as illustrated in FIGS. 9A and 9B, a space between the prisms 201 and 201' on the downstream side of the space adjusting part 200 is kept to have an optimum value so that the collecting points formed by the ± first-order diffracted light fluxes on the pupil plane 6A are positioned within the predetermined ring-belt-shaped area (the TIRF area satisfying the generation condition of the evanescent field). This enables to maintain the generation condition of the evanescent field (the TIRF-condition).

Further, according to such a space adjusting part 200, even if the diffraction angle (branching amount) of the ± first-order diffracted light fluxes is small, the space between the collecting points of the ± first-order diffracted light fluxes on the pupil plane 6A can be set to have a proper value, so that a degree of freedom with respect to the structural pitch of the diffraction grating 13 is high.

Therefore, in the present embodiment, it is possible to use an inexpensive diffraction grating with a coarse structural pitch (a diffraction grating which can be easily manufactured), as the diffraction grating 13.

Further, it is desirable that the above-described controlling device 39 automatically switches the space between the prisms 202 and 202' in accordance with a switching of the light source wavelength so that the space between the collecting points on the pupil plane 6A is kept to have an optimum value. Note that the switching of the space between the prisms 202 and 202' performed by the controlling device 39 is conducted via the adjusting mechanism 200A of the space adjusting part 200.

Note that when the space between the prisms 202 and 202' is changed, the optical lengths of the ± first-order diffracted light fluxes are also changed, so that there is a possibility that the collecting points of the ± first-order diffracted light fluxes are displaced to a front side or a rear side of the pupil plane 6A. Accordingly, the above-described controlling device 39 desirably compensates such a displacement of the collecting points by linking the space between the prisms 202 and 202', and the position of the exit end of the optical fiber 11 in the optical axis AZ direction. Note that the adjustment of the position of the exit end performed by the controlling device 39 is conducted via the position adjusting mechanism 11A (refer to FIG. 1).

Hereinafter, a concrete example of the adjusting mechanism 200A of the space adjusting part 200 will be described.

Figure 10:
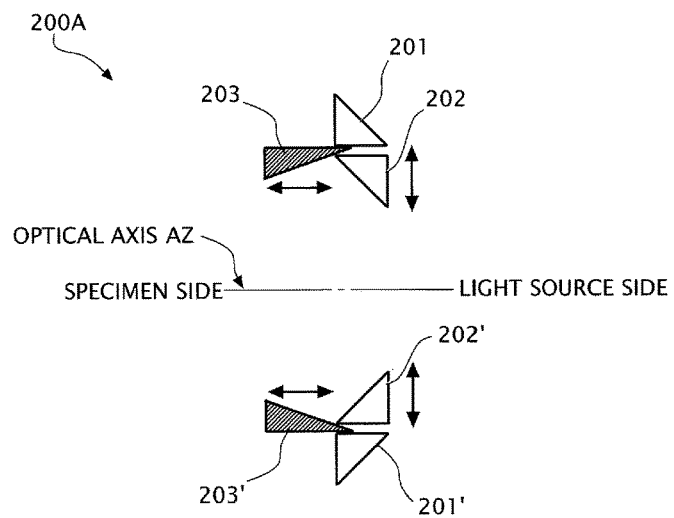
FIG. 10 is a diagram illustrating a relationship of wedge-shaped elements 203 and 203', and prisms 201, 202, 201', and 202'.

FIG. 10 is a diagram illustrating the concrete example of the adjusting mechanism 200A of the space adjusting part 200. The adjusting mechanism 200A illustrated in FIG. 10 includes a wedge-shaped element 203 which is inserted/extracted into/from a part of gap between the prisms 201 and 202 (a position which does not block the optical path), and a wedge-shaped element 203' which is inserted/extracted into/from a part of gap between the prisms 201' and 202' (a position which does not block the optical path).

The wedge-shaped element 203 being one of the wedge-shaped elements is inserted, from the specimen side, into the gap between the prisms 201 and 202, and a thickness of the wedge-shaped element 203 in a direction perpendicular to the optical axis AZ is set in a manner that the closer to the specimen side, the thicker the thickness becomes.

Further, the other wedge-shaped element 203' is inserted, from the specimen side, into the gap between the prisms 201' and 202', and a thickness of the wedge-shaped element 203' in a direction perpendicular to the optical axis AZ is set in a manner that the closer to the specimen side, the thicker the thickness becomes.

Therefore, the larger an insertion amount of each of the wedge-shaped elements 203 and 203', the narrower the space between the prisms 202 and 202' on the upstream side becomes, and the smaller the insertion amount of each of the wedge-shaped elements 203 and 203', the wider the space between the prisms 202 and 202' on the upstream side becomes.

Note that although an illustration is omitted, the adjusting mechanism 200A is also provided with a not-illustrated guide element which controls a moving direction of each of the wedge-shaped elements 203 and 203' to the optical axis AZ direction, a not-illustrated guide element which controls a moving direction of each of the prisms 202 and 202' to a direction perpendicular to the optical axis AZ, a not-illustrated fixing element which fixes the prisms 201 and 201', and the like.

Further, the moving direction and a moving amount of the wedge-shaped element 203 and the moving direction and a moving amount of the wedge-shaped element 203' are mutually common, so that these wedge-shaped elements 203 and 203' may also be configured by a mutually common element. Alternatively, these wedge-shaped elements 203 and 203' may also be mutually fixed.

Incidentally, in the present embodiment, the direction of the interference fringe is switched among the aforementioned three directions (the first direction $V_1$, the second direction $V_2$, and the third direction $V_3$). In order to correspond to this, the space adjusting part 200 previously prepares the above-described prism group (the prisms 201, 202, 201', and 202') and adjusting mechanism 200A, with respect to each of the aforementioned three directions (the first direction $V_1$, the second direction $V_2$, and the third direction $V_3$), as illustrated in FIG. 11.

Figure 11:
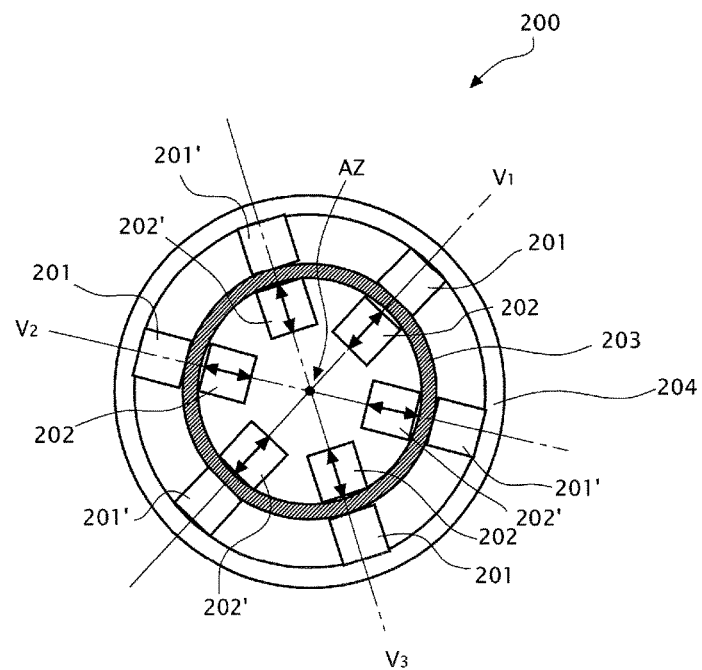
FIG. 11 is a diagram in which an example of the space adjusting part 200 in the first embodiment is seen from an optical axis direction.

Note that FIG. 11 illustrates a diagram in which an example of the space adjusting part 200 is seen from the light source side. In this example, three prism groups (each including the prisms 201, 202, 201', and 202') are disposed, in which one group of the prism groups is a prism group for guiding the ± first-order diffracted light fluxes in which the branching direction is the first direction $V_1$, another group of the prism groups is a prism group for guiding the ± first-order diffracted light fluxes branched along the second direction $V_2$, and the remaining one group of the prism groups is a prism group for guiding the ± first-order diffracted light fluxes branched along the third direction $V_3$.

Further, in this example, the wedge-shaped elements in the respective directions are configured by a common element (a reference numeral 203). Further, an element denoted by a reference numeral 204 in FIG. 11 is a fixing element for fixing the prisms 201 and 201' in the respective directions.

Modified Example of First Embodiment

Note that in the first embodiment, both of the space adjusting part 200 and the beam selecting part 24 are disposed in the vicinity of the same pupil conjugate plane 6A' as illustrated in FIG. 1, but, it is also possible that a relay optical system is inserted into the illuminating optical system 10 to increase a number of the pupil conjugate plane, and the space adjusting part 200 and the beam selecting part 24 are individually disposed in the vicinity of one of mutually different two pupil conjugate planes, and in the vicinity of the other of the pupil conjugate planes.

Note that also in that case, an insertion place of the beam selecting part 24 is desirably at the downstream side of an insertion place of the space adjusting part 200. This is because, if it is set that a disposition place of the beam selecting part 24 is at the downstream side of a disposition place of the space adjusting part 200, incident positions of the ± first-order diffracted light fluxes with respect to the beam selecting element 18 are fixed by the operation of the space adjusting part 200, resulting in that the size of each of the aperture portions of the beam selecting element 18 can be minimized.

Further, in the first embodiment, the number of switching of the light source wavelength is set to two, but, the number may also be increased to three or more. In that case, it is only required to set a number of variable step regarding the space between the prisms 202 and 202' in the space adjusting part 200 to three or more.

Further, although the space adjusting part 200 of the first embodiment previously prepares the prism group (the prisms 201, 202, 201', and 202') with respect to each of the three directions (the first direction $V_1$, the second direction $V_2$, and the third direction $V_3$), it is also possible that the space adjusting part 200 prepares the prism group with respect to only one direction, and is further provided with a mechanism which rotates the entire prism group (the prisms 201, 202, 201', and 202') around the optical axis AZ.

In that case, the above-described controlling device 39 is only required to make a rotating position of the prism group (the prisms 201, 202, 201', and 202') to be linked with the rotating position of the beam selecting element 18.

Figure 12:
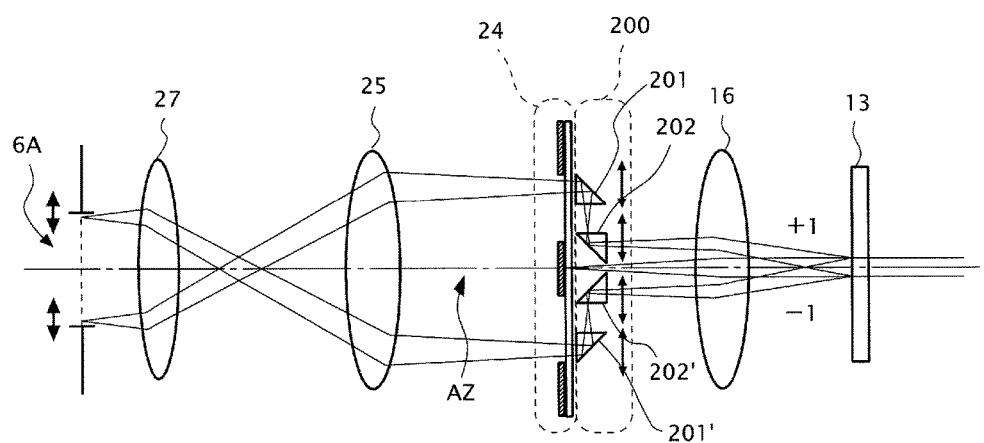
FIG. 12 is a diagram explaining a modified example of the space adjusting part 200 in the first embodiment.

Further, the space adjusting part 200 of the first embodiment enables to vary only the space between the prisms disposed on the upstream side (the prisms 202 and 202'), out of the prisms disposed on the downstream side (the prisms 201 and 201') and the prisms disposed on the upstream side (the prisms 202 and 202'), as indicated by arrows in FIGS. 9A and 9B, but, in addition to that, the space adjusting part 200 may also enable to vary the space between the prisms disposed on the downstream side (the prisms 201 and 201'), as indicated by arrows in FIG. 12.

Note that even in that case, it is desirable to limit an adjustment range of the space between the prisms 201 and 201' to keep the collecting points of the ± first-order diffracted light fluxes to be placed within the ring-belt-shaped area at the outmost circumference of the pupil plane 6A (the area for satisfying the generation condition of the evanescent field).

If it is designed as above, it is possible to perform fine adjustment of a depth of the evanescent field (=a leakage amount of evanescent light with respect to the specimen 5) while maintaining the generation condition of the evanescent field (the TIRF-condition). Concretely, if the space between the prisms 201 and 201' is finely adjusted, the space between the collecting points of the ± first-order diffracted light fluxes is finely adjusted as indicated by arrows at the far left in FIG. 12, so that the incident angles of the ± first-order diffracted light fluxes which are incident on the surface of the specimen 5 are finely adjusted, resulting in that the depth of the evanescent field is finely adjusted.

Further, the above-described controlling device 39 desirably performs the fine adjustment in accordance with an instruction from a user. Accordingly, it becomes possible for the user to freely adjust the depth of the evanescent field.

Further, although the light source wavelength is set to be variable in the first embodiment, when the light source wavelength is invariable, the diffraction angle (branching amount) of the ± first-order diffracted light fluxes that exit from the diffraction grating 13 becomes invariable, so that it is also possible to set such that the space between the prisms on the upstream side (the prisms 202 and 202') is invariable, and only the space between the prisms on the downstream side (the prisms 201 and 201') is variable.

Further, in FIGS. 9A and 9B and FIG. 12 in the first embodiment, a deflection angle of the diffracted light flux (principal ray) in each of the prisms 201 and 201' is set to about 90°, but, it goes without saying that the deflection angle may also be set to an angle deviated from 90°. In like manner, although a deflection angle of the diffracted light flux (principal ray) in each of the prisms 202 and 202' is set to 90° in FIGS. 9A and 9B and FIG. 12, it goes without saying that the deflection angle may also be set to an angle deviated from 90°.

Further, in the first embodiment, the diffraction grating 13 (refer to FIG. 2A) simultaneously generating the plurality of diffracted light flux groups with different branching directions is used as a unit of branching the exit light flux from the light source, but, it is also possible to use a diffraction grating which generates only one group of diffracted light flux group with common branching direction (one-direction diffraction grating). Note that in that case, a mechanism of rotating the one-direction diffraction grating around the optical axis AZ is provided for switching the fringe direction of the structured illuminating light.

Further, in that case, it is also possible to use a 0th-order light blocking mask which does not rotate, instead of the rotatable beam selecting element 18. The 0th-order light blocking mask is a mask having a mask portion arranged on an area capable of being an optical path of high-order diffracted light flux of second-order or higher, having aperture portions arranged on areas capable of being optical paths of the ± first-order diffracted light fluxes, and having a mask portion arranged on an area to be an optical path of the 0th-order diffracted light flux.

Further, in the first embodiment, it is set that the disposition place of the space adjusting part 200 is in the vicinity of the pupil conjugate plane, but, the place may also be a place slightly separated from the pupil conjugate plane, as long as it is a place where the optical paths of the diffracted light fluxes which contribute to the structured illuminating light are mutually separated (a place where the 0th-order diffracted light flux, the + first-order diffracted light flux, and the − first-order diffracted light flux are spatially separated). However, when the place is close to the pupil conjugate plane, a cross section of diffracted light flux which should be reflected by the prism becomes small, which enables to easily secure a movable range of the prism by reducing a size of the prism.

Further, in the first embodiment, the ½ wavelength plate 17 capable of rotating around the optical axis AZ is used to keep the ± first-order diffracted light fluxes which are incident on the specimen 5 to the S polarization, but, it is also possible to use a ¼ wavelength plate disposed in a fixed manner and a ¼ wavelength plate capable of rotating around the optical axis AZ. Note that in that case, a rotating position of the ¼ wavelength plate based on the first reference position is set to a position same as the rotating position of the beam selecting element 18 based on the second reference position.

Further, in the first embodiment, a case where the structured illuminating microscopy apparatus 1 is used as the total internal reflection fluorescence microscopy (TIRFM) is described, but, it is also possible to use the structured illuminating microscopy apparatus 1 as a 3D-structured illumination microscopy (3D-SIM).

Figure 13:
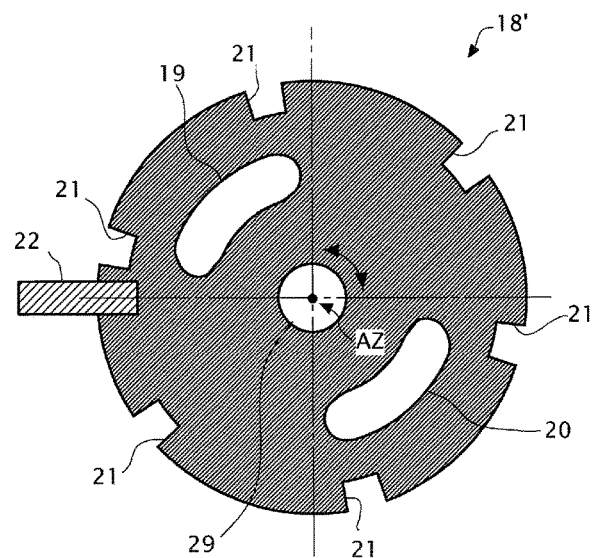
FIG. 13 is a diagram explaining a beam selecting element 18' which is employed when the structured illuminating microscopy apparatus 1 is used as a 3D-SIM.

Note that when the structured illuminating microscopy apparatus 1 is used as the 3D-SIM, there is a requirement that the 0th-order diffracted light flux generated by the diffraction grating 13 is made to be incident on the specimen 5 together with the ± first-order diffracted light fluxes, without being blocked at the pupil conjugate plane 6A'. In order to achieve this, for example, a beam selecting element 18' as illustrated in FIG. 13 may be used, instead of the beam selecting element 18 illustrated in FIG. 6. The beam selecting element 18' corresponds to the beam selecting element 18 illustrated in FIG. 6 in which an aperture portion 29 through which the 0th-order diffracted light flux passes is provided.

Note that a place of formation of the aperture portion 29 is in the vicinity of the optical axis AZ, and a shape of the aperture portion 29 is a circular shape, for example. With the use of such a beam selecting element 18', it is possible to make not only the ± first-order diffracted light fluxes but also the 0th-order diffracted light flux contribute to the interference fringe.

As described above, the interference fringe generated by the interference of three diffracted light fluxes (three-beam interference) are spatially-modulated not only in the plane direction of the specimen 5 but also in the depth direction of the specimen 5. Therefore, with the use of the interference fringe, it becomes possible to obtain the super-resolution effect also in the depth direction of the specimen 5.

Note that when the structured illuminating microscopy apparatus 1 is used as the 3D-SIM, an outer shape of the space adjusting part 200 is set to be appropriately formed so as not to block the optical path of the 0th-order diffracted light flux.

Further, in the 3D-structured illumination microscopy, when the space adjusting part 200 adjusts the space between the prisms 202 and 202' in accordance with the light source wavelength, the super-resolution effect can be kept constant.

Further, in the 3D-structured illumination microscopy, when the space adjusting part 200 adjusts the space between the prisms 201 and 201', the super-resolution effect can be adjusted.

Figure 14:
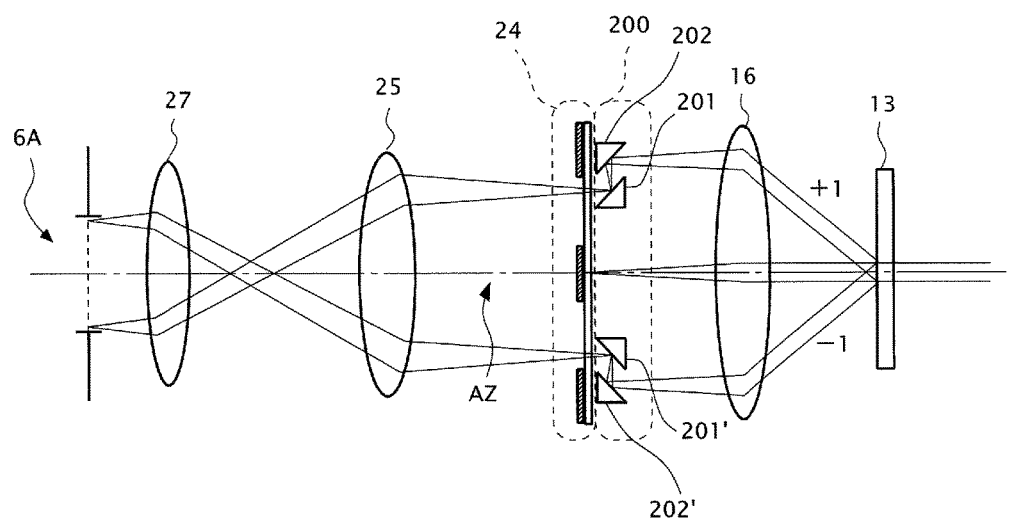
FIG. 14 is a diagram explaining another modified example of the space adjusting part 200.

Further, in the first embodiment, a case where the diffraction angle (branching amount) of the ± first-order diffracted light fluxes at the diffraction grating 13 is relatively small is assumed, and the function of enlarging the space between the optical paths of the ± first-order diffracted light fluxes is given to the space adjusting part 200, as illustrated in FIGS. 9A and 9B and FIG. 12. However, when the diffraction angle (branching amount) of the ± first-order diffracted light fluxes at the diffraction grating 13 is relatively large, a function of narrowing the space between the optical paths of the ± first-order diffracted light fluxes may be given to the space adjusting part 200, as illustrated in FIG. 14.

In that case, the deflection direction of each of the ± first-order diffracted light fluxes deflected by the prisms 202 and 202' on the upstream side becomes, not a direction separating from the optical axis AZ, but a direction approaching the optical axis AZ, so that the prisms 202 and 202' on the upstream side are positioned on a side further inside than the prisms 201 and 201' on the downstream side (a side closer to the optical axis AZ).

Further, although the space adjusting part 200 of the first embodiment uses the prism group (the prisms 201, 202, 201', and 202'), it goes without saying that a reflecting mirror may be used as a part or all of the prisms.

Further, in the first embodiment, when the structured illuminating microscopy apparatus 1 is used as the TIRF-SIM, a combination of the + first-order diffracted light flux and the − first-order diffracted light flux is used as the diffracted light fluxes contributing to the interference fringe, but, it is needless to say that another combination may also be used.

Further, in the first embodiment, when the structured illuminating microscopy apparatus 1 is used as the 3D-SIM, a combination of the + first-order diffracted light flux, the − first-order diffracted light flux, and the 0th-order diffracted light flux is used as the diffracted light fluxes contributing to the interference fringe, but, it is needless to say that another combination may also be used.

Further, although no mention is made regarding an exchange of the objective lens 6 in the above description, when the objective lens 6 is switched among a plurality of objective lenses with different sizes of pupil plane, it is desirable to maintain the super-resolution effect by driving the adjusting mechanism 200A in accordance with the switching of the objective lens 6.

Operation and Effect of First Embodiment

As described above, a structured illuminating apparatus of the first embodiment includes: a branching unit (13) branching an exit light flux from a light source (100) into at least two branched light fluxes; an illuminating optical system (10) making the two branched light fluxes to be respectively collected at mutually different positions on a pupil plane (6A) of an objective lens (6) and making the two branched light fluxes to be interfered with each other on an object-side of the objective lens (6) to illuminate a specimen (5) with an interference fringe of the two branched light fluxes; and an adjusting unit (200) adjusting or controlling a height from an optical axis (AZ) of the illuminating optical system (10) to two collecting points formed on the pupil plane (6A) by the two branched light fluxes, in which the adjusting unit (200) includes an optical element (201, 202, 201', and 202')

deflecting the two branched light fluxes at a deflection angle in accordance with a wavelength of the two branched light fluxes.

Further, the adjusting unit (200) includes a first reflecting surface (202) deflecting an optical path of a first light flux being one of the two branched light fluxes, a second reflecting surface (201) returning a direction of the optical path of the first light flux deflected by the first reflecting surface (202) to an original direction, a third reflecting surface (202') deflecting an optical path of a second light flux being the other of the two branched light fluxes, and a fourth reflecting surface (201') returning a direction of the optical path of the second light flux deflected by the third reflecting surface (202') to an original direction, in which at least one of a positional relationship between the first reflecting surface (202) and the third reflecting surface (202') and a positional relationship between the second reflecting surface (201) and the fourth reflecting surface (201') is variable.

Therefore, the structured illuminating apparatus of the first embodiment can adjust or control a super-resolution effect of a structured illuminating microscopy apparatus (1).

Note that the structured illuminating apparatus of the first embodiment further includes a position adjusting unit (11A) adjusting the positions of the two collecting points in the optical axis (AZ) direction.

Therefore, the structured illuminating apparatus of the first embodiment can deal with a focus deviation which can occur during the adjustment of the super-resolution effect.

Further, the adjusting unit (200) keeps a positional relationship of the two collecting points to a relationship symmetric about the optical axis (AZ).

Therefore, the structured illuminating apparatus of the first embodiment can prevent a deterioration of an interference fringe which can occur during the adjustment of the super-resolution effect.

Further, the branching unit (13) is a diffractive optical element.

As described above, when the diffractive optical element is used as the branching unit (13), a branching amount of the two branched light fluxes depends on a wavelength, so that there was a possibility that the height of each of the two collecting points from the optical axis (AZ) depends on the wavelength, namely, the super-resolution effect depends on the wavelength. However, since the structured illuminating apparatus of the first embodiment includes the adjusting unit (200), it is possible to suppress the wavelength dependency of the super-resolution effect.

Further, the height is adjusted to have a value which falls within a predetermined range, and the predetermined range is a range in which the two branched light fluxes can generate an evanescent field in the vicinity of a surface of the specimen.

Therefore, the structured illuminating apparatus of the first embodiment can prevent a collapse of TIRF-condition which can occur during the adjustment of the super-resolution effect.

Further, the height is finely adjusted within the predetermined range in accordance with an instruction from a user.

Therefore, the user can freely adjust the super-resolution effect within a range in which the TIRF-condition does not collapse.

Further, the light source (100) can switch a wavelength of the exit light flux, and the height is adjusted to have a predetermined value regardless of the switching of the wavelength.

Therefore, the structured illuminating apparatus of the first embodiment can securely suppress the wavelength dependency of the super-resolution effect.

Further, the structured illuminating apparatus of the first embodiment further includes a switching unit (18) switching the positions of the two collecting points among a plurality of rotating positions around the optical axis (AZ), and the adjusting unit (200) is prepared for each of the plurality of rotating positions.

Alternatively, the structured illuminating apparatus of the first embodiment further includes a first switching unit (18) switching the positions of the two collecting points among a plurality of rotating positions around the optical axis (AZ), and a second switching unit switching a position of the adjusting unit (200) among the plurality of rotating positions.

Further, the structured illuminating apparatus of the first embodiment further includes a phase shifting unit (15A) shifting a phase of the interference fringe.

Therefore, the structured illuminating apparatus of the first embodiment can switch the direction and the phase of the interference fringe projected onto the specimen (5).

Further, a structured illuminating microscopy apparatus (1) of the first embodiment includes: any one of the structured illuminating apparatus described above; and an image-forming optical system (30) forming an image on a light detector (35) by an observational light flux from the specimen (5) modulated by the interference fringe.

Therefore, the structured illuminating microscopy apparatus (1) of the first embodiment can perform imaging on a modulated image of the specimen (5).

Further, the structured illuminating microscopy apparatus (1) of the first embodiment further includes a calculating unit (40) calculating a demodulated image of the specimen (5) based on an image generated by the light detector (35).

Therefore, the structured illuminating microscopy apparatus (1) of the first embodiment can obtain a super-resolved image of the specimen (5).

Second Embodiment

Hereinafter, a structured illuminating microscopy apparatus will be described as a second embodiment of the present invention.

First, a configuration of the structured illuminating microscopy apparatus of the present embodiment will be described. A main point of difference between the present embodiment and the first embodiment lies in a configuration and a disposition place of the space adjusting part 200.

Note that according to the space adjusting part 200 of the present embodiment, a simultaneous observation using two types of wavelengths can be carried out, so that in this case, a configuration example of an apparatus for performing the simultaneous observation will be described.

Figure 15:
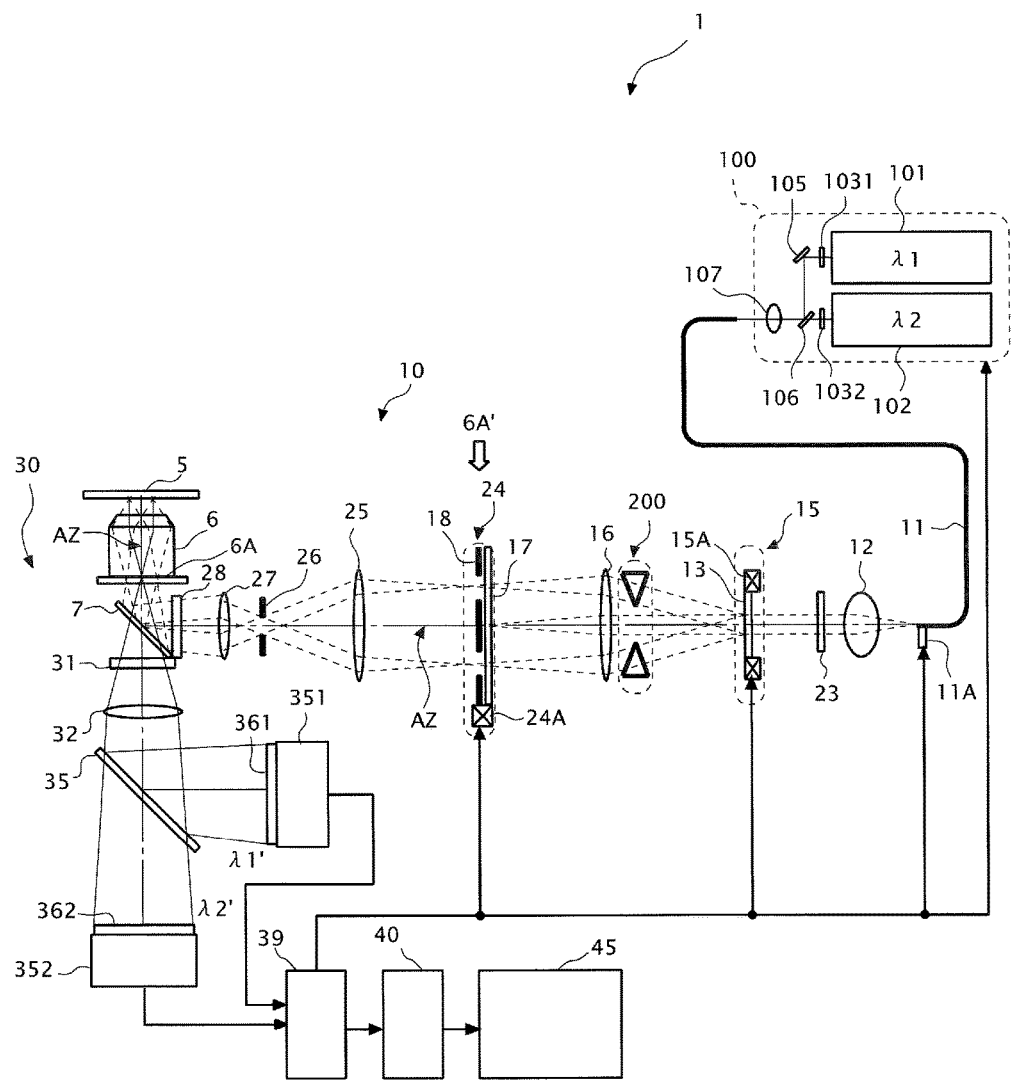
FIG. 15 is a configuration diagram of a structured illuminating microscopy apparatus 1 of a second embodiment.

As illustrated in FIG. 15, there are provided, in a structured illuminating microscopy apparatus 1 of the present embodiment, a laser unit 100, an optical fiber 11, an illuminating optical system 10, an image-forming optical system 30, a first imaging sensor 351, a second imaging sensor 352, a controlling device 39, an image storing-calculating device 40, and an image displaying device 45. Note that the illuminating optical system 10 is one of epi-illumination type, and illuminates a specimen 5 by utilizing an objective lens 6 and a dichroic mirror 7 of the image-forming optical system 30.

In the laser unit 100, there are provided a first laser light source 101, a second laser light source 102, shutters 1031 and 1032, a mirror 105, a dichroic mirror 106, and a lens 107. Each of the first laser light source 101 and the second laser light source 102 is a coherent light source, and exit wavelengths of the laser light sources are mutually different. Here, it is assumed that a wavelength λ1 of the first laser light source 101 is longer than a wavelength λ2 of the second laser light source 102 (λ1>λ2). The first laser light source 101, the second laser light source 102, and the shutters 1031 and 1032 are respectively driven by the controlling device 39.

The optical fiber 11 is formed of, for example, a polarization-maintaining single-mode fiber to guide a laser light exited from the laser unit 100. A position in an optical axis AZ direction of an exit end of the optical fiber 11 can be adjusted by a position adjusting mechanism 11A. The position adjusting mechanism 11A is driven by the controlling device 39.

In the illuminating optical system 10, there are disposed a collector lens 12, a polarizing plate 23, a beam branching part 15, a space adjusting part 200, a collecting lens 16, a beam selecting part 24, a lens 25, a field stop 26, a field lens 27, an excitation filter 28, the dichroic mirror 7, and the objective lens 6, in this order from an exit end side of the optical fiber 11.

The beam branching part 15 is provided with a diffractive optical element (diffraction grating) 13 similar to that of the first embodiment, and a translatory shifting mechanism 15A similar to that of the first embodiment, the space adjusting part 200 is provided with a plurality of prisms (details will be described later), and the beam selecting part 24 is provided with a ½ wavelength plate 17 similar to that of the first embodiment, a beam selecting element 18 similar to that of the first embodiment, and a rotating mechanism 24A similar to that of the first embodiment. Note that the translatory shifting mechanism 15A and the rotating mechanism 24A are driven by the controlling device 39 in a similar manner to the first embodiment.

In the image-forming optical system 30, there are disposed the objective lens 6, the dichroic mirror 7, a barrier filter 31, a secondary objective lens 32, and a second dichroic mirror 35, in this order from a side of the specimen 5.

The specimen 5 is, for example, a culture fluid dropped on a surface of parallel-plate glass, and a cell having a fluorescence (a cell stained by a fluorescent dye) exists in the vicinity of a glass interface in the culture fluid. Both of a first fluorescent area which is excited by a light with the wavelength λ1 and a second fluorescent area which is excited by a light with the wavelength λ2 are exhibited in the cell.

Note that in the first fluorescent area, a first fluorescence with a center wavelength λ1' is generated in accordance with the light with the wavelength λ1, and in the second fluorescent area, a second fluorescence with a center wavelength λ2' is generated in accordance with the light with the wavelength λ2.

The objective lens 6 is configured as an objective lens of immersion type (oil-immersion type) so as to enable a total internal reflection fluorescence observation. Specifically, a gap between the objective lens 6 and the glass of the specimen 5 is filled with immersion liquid (oil).

Each of the first imaging sensor 351 and the second imaging sensor 352 is a two-dimensional imaging sensor formed of a CCD, a CMOS or the like. When the first imaging sensor 351 is driven by the controlling device 39, it captures an image formed on its imaging plane 361 and generates an image, and when the second imaging sensor 352 is driven by the controlling device 39, it captures an image formed on its imaging plane 362 and generates an image. The image generated by each of the first imaging sensor 351 and the second imaging sensor 352 is taken into the image storing-calculating device 40 via the controlling device 39.

The controlling device 39 drives and controls the laser unit 100, the position adjusting mechanism 11A, the translatory shifting mechanism 15A, the rotating mechanism 24A, the first imaging sensor 351, and the second imaging sensor 352.

The image storing-calculating device 40 performs calculation with respect to the image given via the controlling device 39, stores the calculated image in a not-illustrated internal memory, and sends at the same time the image to the image displaying device 45.

Next, a behavior of laser light in the structured illuminating microscopy apparatus 1 will be described.

A laser light with the wavelength λ1 exited from the first laser light source 101 (first laser light) is incident on the mirror 105 via the shutter 1031, and reflected by the mirror 105 to be incident on the dichroic mirror 106. Meanwhile, a laser light with the wavelength λ2 exited from the second laser light source 102 (second laser light) is incident on the dichroic mirror 106 via the shutter 1032, and combined with the first laser light. The first laser light and the second laser light exited from the dichroic mirror 106 are incident on an incident end of the optical fiber 11 via the lens 107.

Note that the controlling device 39 can switch the wavelength (=light source wavelength) of laser light incident on the incident end of the optical fiber 11, between the long wavelength λ1 and the short wavelength λ2, or set the light source wavelength to both of the long wavelength λ1 and the short wavelength λ2, by controlling the shutters 1031 and 1032 of the laser unit 100.

The laser light incident on the incident end of the optical fiber 11 propagates in the optical fiber 11, and generates a point light source at the exit end of the optical fiber 11. The laser light exited from the point light source is converted into a collimated light flux by the collector lens 12 to be incident on the diffraction grating 13 via the polarizing plate 23, and then branched into diffracted light fluxes with respective orders. The diffracted light fluxes with respective orders are incident on the collecting lens 16 via the space adjusting part 200, and then collected by the collecting lens 16 at mutually different positions on a pupil conjugate plane 6A'.

Here, the pupil conjugate plane 6A' indicates a focal position of the collecting lens 16 (rear focal position), and a position conjugated with a pupil 6A of the later-described objective lens 6 (a position at which ± first-order diffracted lights are collected) via the field lens 27 and the lens 25. Note that it is set that a position determined by a person skilled in the art by taking the design requirements such as aberration, vignetting and the like of the objective lens 6, the field lens 27, and the lens 25 into consideration, also falls into the concept of "conjugate position" mentioned here).

Note that since the laser light exited from the optical fiber 11 is basically linearly polarized, the polarizing plate 23 can be omitted, but, the polarizing plate 23 is effective to securely cut an excess polarization component. Further, in order to increase a utilization efficiency of the laser light, an axis of the polarizing plate 23 desirably coincides with a polarization direction of the laser light exited from the optical fiber 11.

The diffracted light fluxes with respective orders directed to the pupil conjugate plane 6A' are incident on the beam selecting part 24 disposed in the vicinity of the pupil conjugate plane 6A'.

Here, the structured illuminating microscopy apparatus 1 of the present embodiment is used as the TIRFM (total internal reflection fluorescence microscopy), so that the beam selecting part 24 makes only a pair of diffracted light fluxes (only ± first-order diffracted light fluxes, in this case) to be selectively passed therethrough out of the incident diffracted light fluxes with respective orders.

The ± first-order diffracted light fluxes passed through the beam selecting part 24 are converted into convergent lights by the field lens 27 after forming a conjugated plane of the diffraction grating 13 in the vicinity of the field stop 26 via the lens 25, are reflected by the dichroic mirror 7 after passing through the excitation filter 28, and are collected at mutually different positions on the pupil plane 6A of the objective lens 6.

The respective ± first-order diffracted light fluxes collected on the pupil plane 6A are turned into collimated light fluxes when being exited from a tip of the objective lens 6, and interfere with each other on a surface of the specimen 5, to thereby form an interference fringe. The interference fringe is used as structured illuminating light.

Further, since the structured illuminating microscopy apparatus 1 of the present embodiment is used as the TIRFM (total internal reflection fluorescence microscopy), an incident angle of the light flux incident on the surface of the specimen 5 satisfies a generation condition of evanescent field (total internal reflection condition). Hereinafter, the total internal reflection condition is referred to as "TIRF-condition".

In order to satisfy the TIRF-condition, collecting points of the ± first-order diffracted light fluxes on the pupil plane 6A are required to be positioned within a predetermined ring-belt-shaped area at an outmost circumference of the pupil plane 6A. The above-described space adjusting part 200 is provided to adjust a space between collecting points of a pair of diffracted light fluxes on the pupil plane 6A, and to set the collecting points of the both diffracted light fluxes to be positioned within the predetermined ring-belt-shaped area (details will be described later). As a result of this adjustment, an evanescent field formed by an interference fringe is generated in the vicinity of the surface of the specimen 5.

When the specimen 5 is illuminated by such interference fringe, a moiré fringe corresponding to a difference between a pitch structure of the interference fringe and a pitch structure of a fluorescent area on the specimen 5 appears, in which on the moiré fringe, a structure of high frequency of the fluorescent area is shifted to a side of frequency that is lower than the original frequency, so that a fluorescence that exhibits this structure is directed to the objective lens 6 at an angle smaller than the original angle. Therefore, when the specimen 5 is illuminated by the interference fringe, even structural information of the high frequency of the fluorescent area is transmitted by the objective lens 6.

The fluorescence generated in the vicinity of the surface of the specimen 5 (evanescent field) is incident on the objective lens 6, and converted into a collimated light by the objective lens 6, and after that, the collimated light transmits through the dichroic mirror 7 and the barrier filter 31, and is then incident on the second dichroic mirror 35. The first fluorescence with the wavelength $\lambda 1'$ incident on the second dichroic mirror 35 is reflected by the second dichroic mirror 35, and the second fluorescence with the wavelength $\lambda 2'$ incident on the second dichroic mirror 35 transmits through the second dichroic mirror 35.

The first fluorescence reflected by the second dichroic mirror 35 forms a modulated image of the first fluorescent area on the imaging plane 361 of the first imaging sensor 351, and the second fluorescence transmitted through the second dichroic mirror 35 forms a modulated image of the second fluorescent area on the imaging plane 362 of the second imaging sensor 352.

The modulated image of the first fluorescent area formed on the imaging plane 361, and the modulated image of the second fluorescent area formed on the imaging plane 362 are individually subjected to imaging by the first imaging sensor 351 and the second imaging sensor 352, resulting in that a modulated image of the first fluorescent area and a modulated image of the second fluorescence are generated.

The modulated image of the first fluorescent area and the modulated image of the second fluorescent area are taken into the image storing-calculating device 40 via the controlling device 39. Further, the image storing-calculating device 40 performs publicly-known demodulating calculation on each of the modulated image of the first fluorescent area and the modulated image of the second fluorescent area taken therein, thereby generating a demodulated image of the first fluorescent area (super-resolved image) and a demodulated image of the second fluorescent area (super-resolved image). Further, these super-resolved images are stored in the internal memory (not illustrated) of the image storing-calculating device 40, and at the same time, they are sent to the image displaying device 45. Note that as the publicly-known demodulating calculation, a method disclosed in specification of U.S. Pat. No. 8,115,806 is employed, for example.

Next, the space adjusting part 200 of the present embodiment will be described in detail.

Figure 16A:
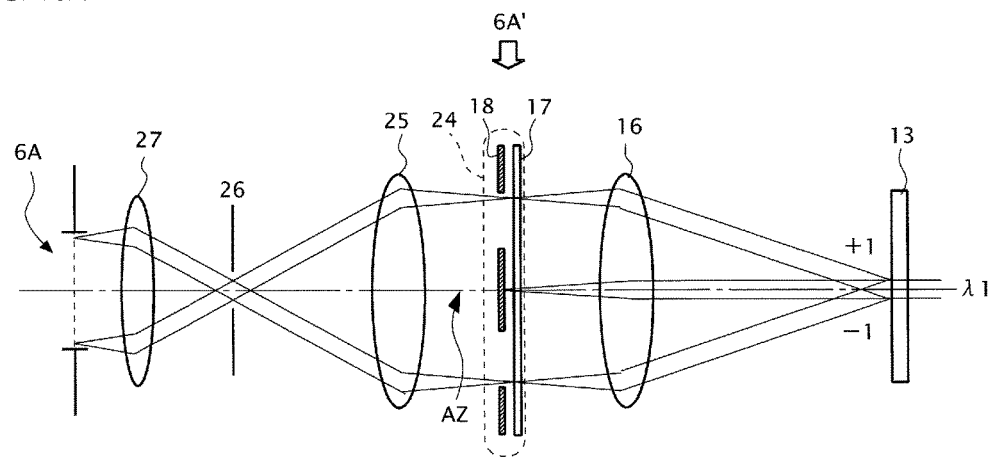
FIGS. 16A and 16B are diagrams illustrating optical paths of an illuminating optical system 10 which does not include a space adjusting part 200.
Figure 16B:
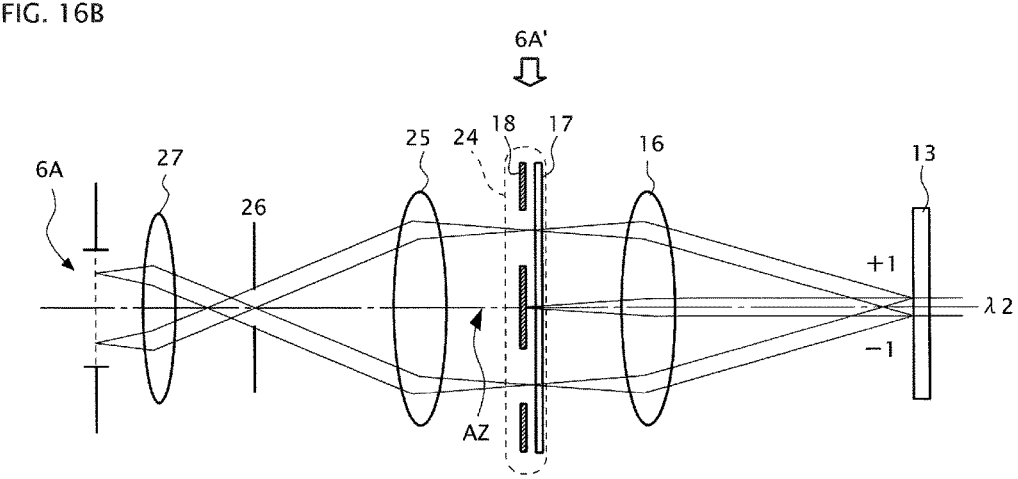
Figure 17A:
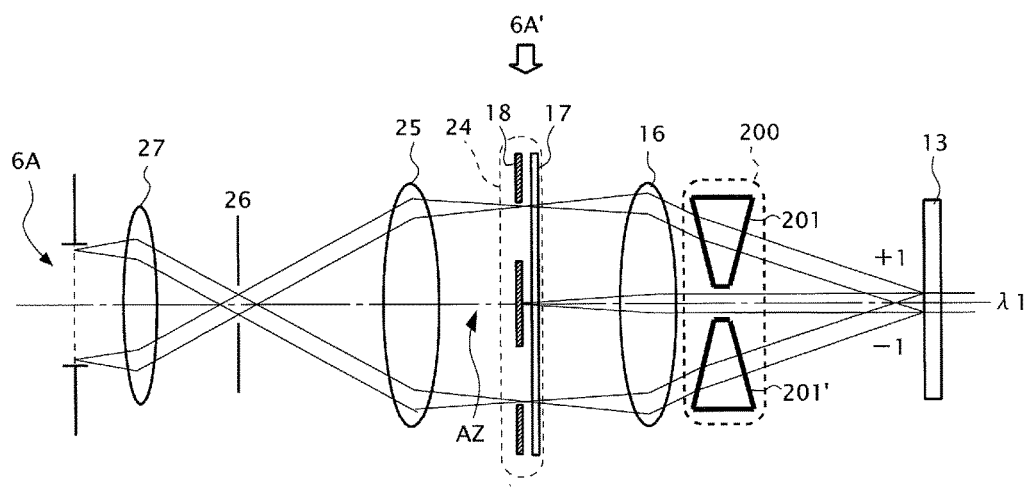
FIGS. 17A and 17B are diagrams illustrating optical paths of the illuminating optical system 10 which includes a space adjusting part 200 of the second embodiment.
Figure 17B:
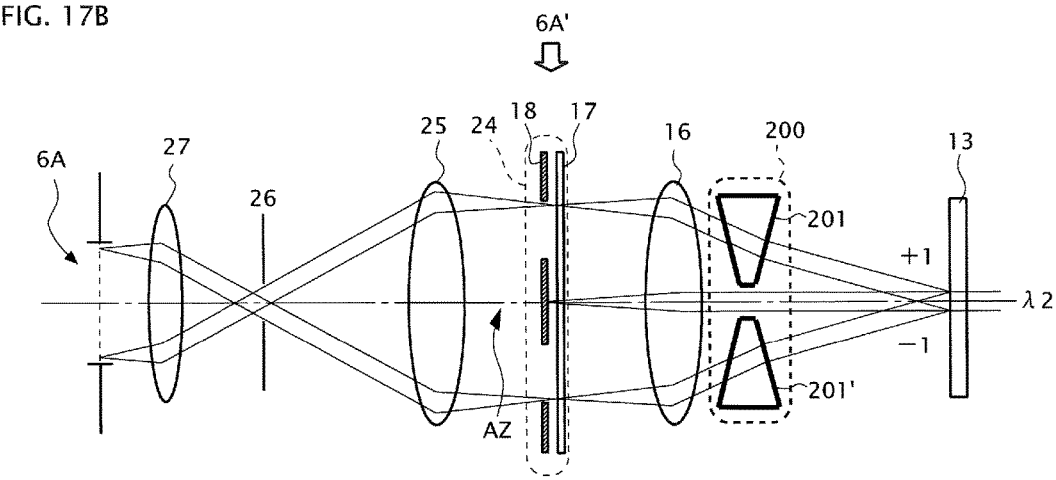

FIGS. 16A and 16B illustrate optical paths of the illuminating optical system 10 when the space adjusting part 200 is not provided, and FIGS. 17A and 17B illustrate optical paths of the illuminating optical system 10 when the space adjusting part 200 is provided. Each of FIG. 16A and FIG. 17A illustrates a case where a light source wavelength is a long wavelength $\lambda 1$, and each of FIG. 16B and FIG. 17B illustrates a case where the light source wavelength is a short wavelength $\lambda 2$. Note that an illustration of the excitation filter 28 and the dichroic mirror 7 is omitted in FIGS. 16A and 16B and FIGS. 17A and 17B.

When the case where the light source wavelength is the long wavelength $\lambda 1$ and the case where the light source wavelength is the short wavelength $\lambda 2$ are compared, a diffraction angle (branching amount) of the ± first-order diffracted light fluxes which exit from the diffraction grating 13 is different, so that if, tentatively, the space adjusting part 200 is not provided as illustrated in FIGS. 16A and 16B, a height of each of collecting points of the ±first-order diffracted light fluxes on the pupil plane 6A becomes different (a space between the collecting points of the ± first-order diffracted light fluxes becomes different). Note that here, a distance from the optical axis AZ to a light ray is simply referred to as "height".

If the height of the collecting point becomes different between the wavelengths $\lambda 1$ and $\lambda 2$ as above, a super-resolution effect also becomes different between the wavelengths $\lambda 1$ and $\lambda 2$. The super-resolution effect is a ratio of a resolving power when modulation is performed (a resolving power achieved by the structured illuminating light), based on a resolving power when no modulation is performed (a resolving power achieved by a uniform illuminating light), and the larger the ratio of the height of the collecting point with respect to a pupil radius of the objective lens 6, the higher the super-resolution effect becomes.

Further, when the height of the collecting point becomes different between the wavelengths $\lambda 1$ and $\lambda 2$, there is a possibility that the collecting points in both cases where the wavelength is λ1 and where the wavelength is λ2 cannot be positioned within the TIRF area. The TIRF area indicates the predetermined ring-belt-shaped area positioned at the outmost circumference of the pupil plane 6A, and if the collecting points are not positioned within the TIRF area, the TIRF-condition cannot be satisfied, resulting in that the total internal reflection observation cannot be conducted.

Accordingly, in the present embodiment, the space adjusting part 200 as illustrated in FIGS. 17A and 17B (refer to FIGS. 17A and 17B) is employed.

First, a disposition place of the space adjusting part 200 is a place, on an optical path from the diffraction grating 13 to the pupil plane 6A, in which a 0th-order diffracted light flux, a + first-order diffracted light flux, and a − first-order diffracted light flux are spatially separated, and a place separated from the pupil plane 6A or the pupil conjugate plane 6A'. Incidentally, if the disposition place of the space adjusting part 200 is too close to the pupil plane 6A or the pupil conjugate plane 6A', a function of the space adjusting part 200 cannot be fully exhibited.

Further, the disposition place of the space adjusting part 200 is desirably a place where each of the + first-order diffracted light flux and the − first-order diffracted light flux becomes a collimated light flux (a place between the diffraction grating 13 and the collecting lens 16, a place between the lens 25 and the field lens 27), compared to a place where each of the + first-order diffracted light flux and the − first-order diffracted light flux becomes a collected light flux or a divergent light flux (a place between the collecting lens 16 and the lens 25, a place between the field lens 27 and the pupil plane 6A). This is because such a disposition makes it easy to design the space adjusting part 200.

Further, the disposition place of the space adjusting part 200 may be either a place where the + first-order diffracted light flux and the − first-order diffracted light flux propagate while separating from each other (a place between the diffraction grating 13 and the collecting lens 16, a place between the field stop 26 and the field lens 27), or a place where the + first-order diffracted light flux and the − first-order diffracted light flux propagate while approaching each other (a place between the lens 25 and the field stop 26). The disposition place between the above two places may be appropriately selected in accordance with a disposition space in the illuminating optical system 10.

Here, the disposition place of the space adjusting part 200 is assumed to be a place between the diffraction grating 13 and the collecting lens 16, as illustrated in FIGS. 17A and 17B. The disposition place is a place where each of the + first-order diffracted light flux and the − first-order diffracted light flux becomes a collimated light flux, and the + first-order diffracted light flux and the − first-order diffracted light flux propagate while separating from each other.

Meanwhile, the space adjusting part 200 is provided with a refractive element (prism) 201 inserted into an independent optical path of the + first-order diffracted light flux, and a refractive element (prism) 201' inserted into an independent optical path of the − first-order diffracted light flux. A material of the prism 201 and a material of the prism 201' are mutually the same, and a relationship between a shape of the prism 201 and a shape of the prism 201' is symmetric about the optical axis AZ. Accordingly, there is no possibility that the symmetry of the + first-order diffracted light flux and the − first-order diffracted light flux about the optical axis AZ is lost due to the disposition of the space adjusting part 200.

Further, a thickness in the optical axis AZ direction of each of the pair of prisms 201 and 201' is set to be increased as a distance from the optical axis AZ increases. In this case, the + first-order diffracted light flux and the − first-order diffracted light flux which propagate while separating from each other are deflected in directions in which a separation amount between the both light fluxes is further increased (directions separating from the optical axis AZ).

In this case, an angle of each of the ± first-order diffracted light fluxes directed to the collecting lens 16 becomes large. Although there is a difference in an enlargement amount of the angle between the wavelength λ1 and the wavelength λ2, an angle of light ray is enlarged in both of cases where the wavelength is λ1 and where the wavelength is λ2. Note that here, an angle made by the light ray with the optical axis AZ is simply referred to as "angle".

Therefore, the pair of prisms 201 and 201' have a function of deflecting the ± first-order diffracted light fluxes in the directions of enlarging the height of each of the collecting points on the pupil conjugate plane 6A' (furthermore, the height of each of the collecting points on the pupil plane 6A).

Here, a material of each of the pair of prisms 201 and 201' is a glass, for example, and a value of a refractive index of the glass with respect to the short wavelength λ2 is larger than that with respect to the light with the long wavelength λ1. For this reason, a value of the deflection angle with the use of the pair of prisms 201 and 201' with respect to the short wavelength λ2 (refer to FIG. 17B) becomes larger than that with respect to the long wavelength λ1 (refer to FIG. 17A).

In this case, an angle of light ray with the short wavelength λ2 exited at a small angle from the diffraction grating 13 is approximated to an angle of light ray with the long wavelength λ1 exited at a large angle from the diffraction grating 13.

Therefore, the height of each of the collecting points on the pupil conjugate plane 6A' (furthermore, the height of each of the collecting points on the pupil plane 6A) when the wavelength is λ1, and that when the wavelength is λ2 can be approximated to each other by the pair of prisms 201 and 201'.

Note that as a material of each of the pair of prisms 201 and 201', it is desirable to use a material in which a dispersion with respect to the wavelengths λ1 and λ2 is as high as possible (high-dispersion glass). By designing as above, it is possible to increase a difference of deflection angles given to the wavelengths λ1 and λ2 by the pair of prisms 201 and 201'.

By utilizing this, in the present embodiment, the difference of deflection angles given to the wavelengths λ1 and λ2 by the pair of prisms 201 and 201' is set to have a value by which a difference of diffraction angles given to the wavelengths λ1 and λ2 by the diffraction grating 13 is cancelled.

In this case, the angle of light ray with the short wavelength 22 exited at the small angle from the diffraction grating 13 coincides with the angle of light ray with the long wavelength λ1 exited at the large angle from the diffraction grating 13, so that the height of each of the collecting points on the pupil conjugated plane 6A' (furthermore, the height of each of the collecting points on the pupil plane 6A) becomes common between the wavelengths λ1 and λ2.

Therefore, in the present embodiment, the super-resolution effect becomes common between the wavelengths λ1 and λ2.

Besides, in the present embodiment, the level of the deflection angles given to both of the wavelengths λ1 and λ2 by the pair of prisms 201 and 201' is set to have a value which enables the collecting points on the pupil plane 6A to be positioned within the TIRF area.

Therefore, in the present embodiment, it is possible to conduct the total internal reflection observation in both cases where the wavelength is λ1 and where the wavelength is λ2.

Note that in the present embodiment, a posture of each of the pair of prisms 201 and 201' is desirably set to make an incident angle of light ray which is incident on each of the pair of prisms 201 and 201' become approximately 0°. By designing as above, it is possible to increase the deflection angles of light rays with the use of the pair of prisms 201 and 201', so that a prism with a small vertex angle can be used as each of the pair of prisms 201 and 201'.

Further, when the deflection angle given to the light ray by each of the pair of prisms 201 and 201' is increased as in the present embodiment, even if the diffraction angle (branching amount) given to the light ray by the diffraction grating 13 is tentatively small, the height of each of the collecting points on the pupil plane 6A can be increased, so that a diffraction grating with a coarse structural pitch can be used as the diffraction grating 13.

Further, in the present embodiment, a disposition place of the space adjusting part 200 is set to an upstream side of a disposition place of the beam selecting element 18, so that an incident position of light ray with respect to the beam selecting element 18 is unchanged between the wavelengths λ1 and λ2. Therefore, in the present embodiment, a size in the height direction of each of the aperture portions 19 and 20 formed on the beam selecting element 18 can be minimized.

Incidentally, in the present embodiment, the direction of an interference fringe is switched among the aforementioned three directions (the first direction $V_1$, the second direction $V_2$, and the third direction $V_3$). In order to correspond to this, the space adjusting part 200 is set to previously prepare the above-described pair of prisms 201 and 201' for each of the aforementioned three directions (the first direction $V_1$, the second direction $V_2$, and the third direction $V_3$), as illustrated in FIG. 18.

Figure 18:
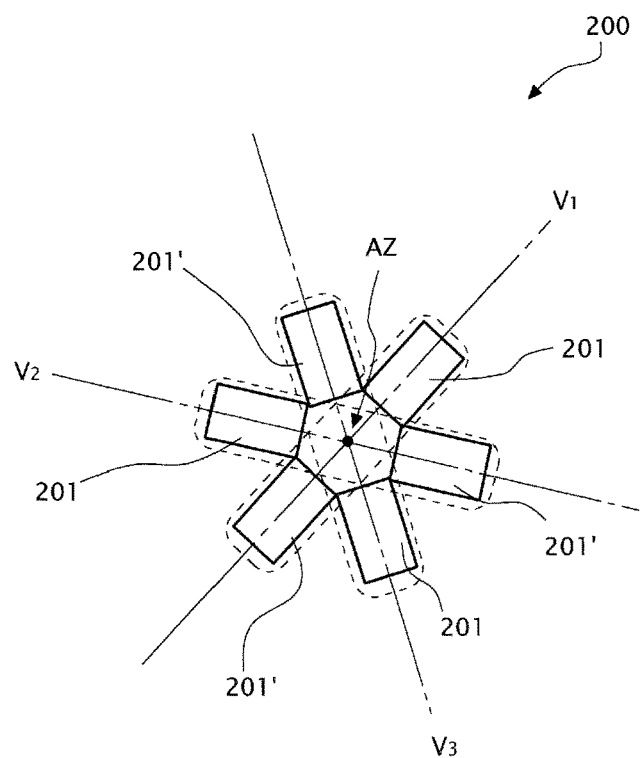
FIG. 18 is a diagram in which an example of the space adjusting part 200 in the second embodiment is seen from an optical axis direction.

Note that FIG. 18 illustrates a diagram in which an example of the space adjusting part 200 is seen from the light source side. In this example, the pair of prisms 201 and 201' are disposed along each of the three directions (the first direction $V_1$, the second direction $V_2$, and the third direction $V_3$), in which a certain pair of prisms out of the above correspond to prisms for guiding the ± first-order diffracted light fluxes branched along the first direction $V_1$, another pair of prisms correspond to prisms for guiding the ± first-order diffracted light fluxes branched along the second direction $V_2$, and the remaining one pair of prisms correspond to prisms for guiding the ± first-order diffracted light fluxes in which the branching direction is the third direction $V_3$.

Modified Example of Second Embodiment

Note that in the second embodiment, although the disposition place of the space adjusting part 200 is set to a place between the diffraction grating 13 and the collecting lens 16 as illustrated in FIG. 15, it may also be set to a place between the field stop 26 and the field lens 27.

However, in that case, the disposition place of the space adjusting part 200 is positioned on the downstream side of the disposition place of the beam selecting element 18, so that the incident positions of the ± first-order diffracted light fluxes with respect to the beam selecting element 18 are displaced between the wavelengths λ1 and λ2.

Accordingly, in that case, each of the aperture portions 19 and 20 of the beam selecting element 18 is required to have a large size in the height direction.

Further, in the second embodiment, the disposition place of the space adjusting part 200 is set to a place where the + first-order diffracted light flux and the – first-order diffracted light flux propagate while separating from each other, but, it may also be set to a place where the + first-order diffracted light flux and the – first-order diffracted light flux propagate while approaching each other (a place between the lens 25 and the field stop 26).

Note that in that case, the thickness in the optical axis AZ direction of each of the pair of prisms 201 and 201' is set to be reduced as the distance from the optical axis AZ increases. Specifically, in that case, the shape of each of the pair of prisms 201 and 201' is inverted. Such a pair of prisms 201 and 201' deflect the + first-order diffracted light flux and the – first-order diffracted light flux which propagate while approaching each other, in directions in which a separation amount between the both light fluxes is further reduced (directions approaching the optical axis AZ).

Further, although the space adjusting part 200 of the second embodiment prepares the three sets of the pair of prisms 201 and 201' to deal with the switching of the direction of the interference fringe (refer to FIG. 18), a part or all of the prisms may also be configured by a common element. For example, it is also possible to configure all of the prisms by using one ring-shaped element.

Further, although the space adjusting part 200 of the second embodiment prepares the three sets of the pair of prisms 201 and 201' to deal with the switching of the direction of the interference fringe (refer to FIG. 18), it is also possible that the space adjusting part 200 prepares only one set of the pair of prisms 201 and 201', and the space adjusting part 200 further includes a mechanism of rotating the entire pair of prisms 201 and 201' around the optical axis AZ.

In that case, the above-described controlling device 39 is only required to make a rotating position of the pair of prisms 201 and 201' to be linked with the rotating position of the beam selecting part 18.

Further, in the second embodiment, the diffraction grating 13 which simultaneously generates a plurality of diffracted light flux groups with different branching directions (refer to FIG. 2A) is used as a unit of branching the exit light flux from the light source, but, it is also possible to use a diffraction grating which generates only one group of diffracted light flux group with a common branching direction (one-direction diffraction grating). Note that in that case, a mechanism of rotating the one-direction diffraction grating around the optical axis AZ is provided for switching the direction of the interference fringe.

Further, in that case, it is also possible to use a 0th-order light blocking mask which does not rotate, instead of the rotatable beam selecting part 18. The 0th-order light blocking mask is a mask having a mask portion arranged on an area to be an optical path of high-order diffracted light flux of second-order or higher, having aperture portions arranged on areas to be optical paths of the ± first-order diffracted light fluxes, and having a mask portion arranged on an area to be an optical path of the 0th-order diffracted light flux.

Further, in the second embodiment, the ½ wavelength plate 17 capable of rotating around the optical axis AZ is used to keep the ± first-order diffracted light fluxes which are incident on the specimen 5 to the S polarization, but, it is also possible to use a ¼ wavelength plate disposed in a fixed manner and a ¼ wavelength plate capable of rotating around the optical axis AZ. Note that in that case, a rotating position of the ¼ wavelength plate based on the first reference position is set to a position same as the rotating position of the beam selecting element 18 based on the second reference position.

Further, in the second embodiment, a case where the structured illuminating microscopy apparatus 1 is used as the total internal reflection fluorescence microscopy (TIRFM) is described, but, it is also possible to use the structured illuminating microscopy apparatus 1 as a 3D-structured illumination microscopy (3D-SIM).

Note that when the structured illuminating microscopy apparatus 1 is used as the 3D-SIM, there is a requirement that the 0th-order diffracted light flux generated by the diffraction grating 13 is made to be incident on the specimen 5 together with the ± first-order diffracted light fluxes, without being blocked at the pupil conjugate plane 6A'. In order to achieve this, for example, a beam selecting element 18' as illustrated in FIG. 13 may be used, instead of the beam selecting element 18 illustrated in FIG. 6. The beam selecting element 18' corresponds to the beam selecting element 18 illustrated in FIG. 6 in which an aperture portion 29 through which the 0th-order diffracted light flux passes is provided.

Note that a place of formation of the aperture portion 29 is in the vicinity of the optical axis AZ, and a shape of the aperture portion 29 is a circular shape, for example. With the use of such a beam selecting element 18', it is possible to make not only the ± first-order diffracted light fluxes but also the 0th-order diffracted light flux contribute to the interference fringe.

As described above, the interference fringe generated by the interference of three diffracted light fluxes (three-beam interference) are spatially-modulated not only in the plane direction of the specimen 5 but also in the depth direction of the specimen 5. Therefore, with the use of the interference fringe, it becomes possible to obtain the super-resolution effect also in the depth direction of the specimen 5.

Note that when the structured illuminating microscopy apparatus 1 is used as the 3D-SIM, an outer shape of each of the pair of prisms 201 and 201' is set to be appropriately formed so as not to block the optical path of the 0th-order diffracted light flux. Note that an angle of the 0th-order diffracted light flux which exits from the diffraction grating 13 becomes zero in both cases where the wavelength is λ1 and where the wavelength is λ2, so that there is no need to dispose a prism on the optical path of the 0th-order diffracted light flux.

Further, in the second embodiment, when the structured illuminating microscopy apparatus 1 is used as the TIRF-SIM, a combination of the + first-order diffracted light flux and the − first-order diffracted light flux is used as the diffracted light fluxes contributing to the interference fringe, but, it is needless to say that another combination may also be used.

Further, in the second embodiment, when the structured illuminating microscopy apparatus 1 is used as the 3D-SIM, a combination of the + first-order diffracted light flux, the − first-order diffracted light flux, and the 0th-order diffracted light flux is used as the diffracted light fluxes contributing to the interference fringe, but, it is needless to say that another combination may also be used.

Further, in the second embodiment, the number of the light source wavelength is set to "two", and the number of the imaging sensor is set to "two", so that it is possible to simultaneously excite two types of fluorescences to simultaneously capture two types of fluorescence modulated images. However, in the second embodiment, there is no problem even if it is designed such that the number of the imaging sensor is set to one, and two types of fluorescences are sequentially excited to sequentially capture two types of fluorescence modulated images.

Further, in the second embodiment, the number of the light source wavelength is set to "two", but, it goes without saying that the number may also be increased to three or more.

Further, in the second embodiment, only one space adjusting part 200 is provided, but, when the objective lens 6 is switched among a plurality of objective lenses with different sizes of pupil plane, it is only required to prepare the space adjusting part 200 for each of the objective lenses, and to switch the space adjusting part 200 in accordance with the switching of the objective lens 6.

Operation and Effect of Second Embodiment

As described above, a structured illuminating apparatus of the second embodiment includes: a diffractive optical element (13) branching an exit light flux from a light source (100) into at least two branched light fluxes; an illuminating optical system (10) making the two branched light fluxes to be respectively collected at mutually different positions on a pupil plane (6A) of an objective lens (6) and making the two branched light fluxes to be interfered with each other on an object-side of the objective lens (6) to illuminate a specimen (5) with an interference fringe of the two branched light fluxes; and an adjusting unit (200) adjusting or controlling a height from an optical axis (AZ) of the illuminating optical system (10) to two collecting points formed on the pupil plane (6A) by the two branched light fluxes, in which the adjusting unit (200) includes an optical element (201 and 201') deflecting the two branched light fluxes at a deflection angle in accordance with a wavelength of the two branched light fluxes.

Further, the adjusting unit (200) sets the height from the optical axis (AZ) to the two collecting points formed on the pupil plane (6A) by the two branched light fluxes between at least two types of the exit light fluxes with different wavelengths (λ1 and λ2) approximately the same.

Concretely, the adjusting unit (200) deflects each of the two branched light fluxes, and a difference of deflection angles given to the two types of the exit light fluxes by the adjusting unit (200) is set to a value by which a difference of diffraction angles given to the two types of the exit light fluxes by the diffractive optical element (13) is cancelled.

Further, a disposition place of the adjusting unit (200) is a place where the two branched light fluxes are spatially separated.

Further, the adjusting unit (200) includes a refractive element (201 and 201') disposed at a place where the two branched light fluxes propagate while separating from each other, and a thickness in the optical axis (AZ) direction of the refractive element is set to be increased as a distance from the optical axis (AZ) increases.

Alternatively, the adjusting unit (200) includes a refractive element (not illustrated) disposed at a place where the two branched light fluxes propagate while approaching each other, and a thickness in the optical axis (AZ) direction of the refractive element (not illustrated) is set to be reduced as a distance from the optical axis (AZ) increases.

Therefore, the structured illuminating apparatus of the second embodiment can set the super-resolution effect to be common between the two types of exit light fluxes (λ1 and λ2).

Note that the light source (100) makes the two types of the exit light fluxes ($\lambda 1$ and $\lambda 2$) exit simultaneously or sequentially.

Therefore, the structured illuminating apparatus of the second embodiment can perform illumination with the use of the two types of exit light fluxes ($\lambda 1$ and $\lambda 2$) simultaneously or sequentially.

Further, the structured illuminating apparatus of the second embodiment further includes a switching unit (18) switching the positions of the two collecting points among a plurality of rotating positions around the optical axis (AZ), and the adjusting unit (200) is prepared for each of the plurality of rotating positions.

Alternatively, the structured illuminating apparatus of the second embodiment further includes a first switching unit (18) switching the positions of the two collecting points among a plurality of rotating positions around the optical axis (AZ), and a second switching unit (not illustrated) switching a position of the adjusting unit (200) among the plurality of rotating positions.

Further, the structured illuminating apparatus of the second embodiment further includes a phase shifting unit (15A) shifting a phase of the interference fringe.

Therefore, the structured illuminating apparatus of the second embodiment can switch the direction and the phase of the interference fringe projected onto the specimen (5).

Further, a structured illuminating microscopy apparatus (1) of the second embodiment includes: any one of the structured illuminating apparatus described above; and an image-forming optical system (30) forming an image on a light detector (351 and 352) by an observational light flux from the specimen (5) modulated by the interference fringe.

Therefore, the structured illuminating microscopy apparatus (1) of the second embodiment can perform imaging on modulated images of the specimen (5).

Further, the structured illuminating microscopy apparatus (1) of the second embodiment further includes a calculating unit (40) calculating a demodulated image of the specimen (5) based on an image generated by the light detector (351 and 352).

Therefore, the structured illuminating microscopy apparatus (1) of the second embodiment can obtain super-resolved images of the specimen (5).

Third Embodiment

Hereinafter, a modified example of the second embodiment will be described as a third embodiment of the present invention. Here, only a point of difference between the present embodiment and the second embodiment will be described. The point of difference lies in the configuration of the space adjusting part 200.

Figure 19:
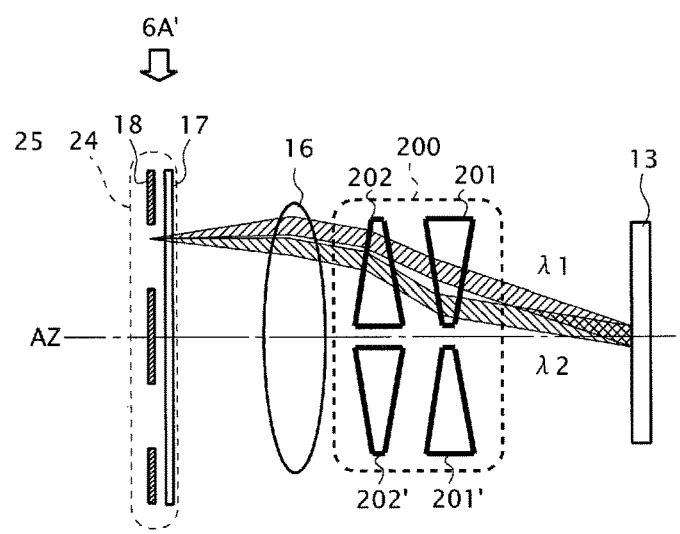
FIG. 19 is a diagram explaining a space adjusting part 200 of a third embodiment.

FIG. 19 is a diagram explaining a space adjusting part 200 of the third embodiment. Note that in FIG. 19, an illustration of the − first-order diffracted light flux is omitted, and the + first-order diffracted light flux with the long wavelength $\lambda 1$ and the + first-order diffracted light flux with the short wavelength $\lambda 2$ are illustrated at the same time. In FIG. 19, a light flux exited at a large angle from the diffraction grating 13 corresponds to the + first-order diffracted light flux with the long wavelength $\lambda 1$, and a light flux exited at a small angle from the diffraction grating 13 corresponds to the + first-order diffracted light flux with the short wavelength $\lambda 2$.

As illustrated in FIG. 19, the space adjusting part 200 of the present embodiment includes, in addition to the pair of prisms 201 and 201', a pair of supplementary refractive elements (prisms) 202 and 202', and the prisms 201 and 201' and the prisms 202 and 202' are disposed one by one in a mutually serial manner.

First, the pair of prisms 201 and 201' disposed on the upstream side have shapes symmetric about the optical axis AZ, and are made of mutually the same material. A disposition place of the prism 201 being one of the pair of prisms is an optical path of the + first-order diffracted light flux, and a disposition place of the other prism 201' is an optical path of the − first-order diffracted light flux. A thickness in the optical axis AZ direction of each of the prisms 201 and 201' is set to be increased as a distance from the optical axis AZ increases. Such a pair of prisms 201 and 201' have functions of deflecting the ± first-order diffracted light fluxes in directions in which a separation amount between the both light fluxes is further increased, similar to the pair of prisms in the second embodiment.

Note that it is assumed that a difference of deflection angles given to the wavelengths $\lambda 1$ and $\lambda 2$ by the pair of prisms 201 and 201' in the present embodiment is larger than that in the second embodiment, and an angle of light ray with the short wavelength $\lambda 2$ becomes larger than an angle of light ray with the long wavelength $\lambda 1$ right after the light rays are exited from the pair of prisms 201 and 201'. For this reason, as a material of the pair of prisms 201 and 201' in the present embodiment, a material in which a dispersion with respect to the wavelengths $\lambda 1$ and $\lambda 2$ is as high as possible, is desirably employed.

Next, the pair of prisms 202 and 202' disposed on the downstream side have shapes symmetric about the optical axis AZ, and are made of mutually the same material. A disposition place of the prism 202 being one of the pair of prisms is an optical path of the + first-order diffracted light flux, and a disposition place of the other prism 202' is an optical path of the − first-order diffracted light flux. A thickness in the optical axis AZ direction of each of the prisms 202 and 202' is set to be reduced as a distance from the optical axis AZ increases. Such a pair of prisms 202 and 202' have functions of setting both of an angle of the wavelength $\lambda 1$ and an angle of the wavelength $\lambda 2$ to have small values, by suppressing angles of the ± first-order diffracted light fluxes, particularly, by strongly suppressing the angle of the short wavelength $\lambda 2$. For this reason, as a material of the pair of prisms 202 and 202', a material in which a dispersion with respect to the wavelengths $\lambda 1$ and $\lambda 2$ is as low as possible, is desirably employed.

Therefore, in the present embodiment, the angle of light ray which is incident on the collecting lens 16 is set to have a small value in both cases where the wavelength is $\lambda 1$ and where the wavelength is $\lambda 2$.

Therefore, in the present embodiment, an effect similar to that of the second embodiment can be achieved, and in addition to that, a further effect such that a lens with weak refractive power can be used as the collecting lens 16, can also be achieved.

Note that in the present embodiment, if a material in which the dispersion is higher than that of the material of the prisms 201 and 201' on the upstream side, is used as the material of the prisms 202 and 202' on the downstream side, the functions of the prisms 201 and 201' on the upstream side are hindered.

Accordingly, in the present embodiment, in order to make good use of the functions of the prisms 201 and 201' on the upstream side, a material in which the dispersion is lower than that of the material of the prisms 201 and 201' on the upstream side, is desirably employed as the material of the prisms 202 and 202' on the downstream side.

Modified Example of Third Embodiment

Note that the third embodiment can also be modified in a similar manner to the second embodiment.

For example, the disposition place of the space adjusting part 200 in the third embodiment can be changed in a similar manner to that of the second embodiment.

For example, when the disposition place of the space adjusting part 200 in the third embodiment is set to a place where the + first-order diffracted light flux and the − first-order diffracted light flux propagate while approaching each other (a place between the lens 25 and the field stop 26), it is only required to invert the shape of each of the prisms 201, 201', 202, and 202'. Specifically, the thickness in the optical axis AZ direction of each of the pair of prisms 201 and 201' is set to be reduced as the distance from the optical axis AZ increases, and the thickness in the optical axis AZ direction of each of the pair of prisms 202 and 202' is set to be increased as the distance from the optical axis AZ increases.

Further, in the space adjusting part 200 of the third embodiment, there is no problem even if the disposition place of the prisms 201 and 201' on the upstream side and the disposition place of the prisms 202 and 202' on the downstream side are made to be opposite.

Operation and Effect of Third Embodiment

As described above, an adjusting unit (200) of the third embodiment includes a refractive element (201 and 201') disposed at a place where two branched light fluxes propagate while separating from each other, and a supplementary refractive element (202 and 202') disposed in front of or behind the refractive element (201 and 201') and having a dispersion weaker than that of the refractive element (201 and 201'), in which a thickness in the optical axis (AZ) direction of the supplementary refractive element (202 and 202') is set to be reduced as a distance from the optical axis (AZ) increases.

Alternatively, an adjusting unit (not illustrated) of the third embodiment includes a refractive element (not illustrated) disposed at a place where two branched light fluxes propagate while approaching each other, and a supplementary refractive element (not illustrated) disposed in front of or behind the refractive element (not illustrated) and having a dispersion weaker than that of the refractive element (not illustrated), in which a thickness in the optical axis (AZ) direction of the supplementary refractive element (not illustrated) is set to be increased as a distance from the optical axis (AZ) increases.

Therefore, in the third embodiment, an effect similar to that of the second embodiment can be achieved, and in addition to that, a further effect such that a lens with weak refractive power can be used as a collecting lens (16) for forming collecting points, can also be achieved.

Fourth Embodiment

Hereinafter, a modified example of the second embodiment will be described as a fourth embodiment of the present invention. Here, only a point of difference between the present embodiment and the second embodiment will be described. The point of difference lies in the configuration of the space adjusting part 200.

Figure 20:
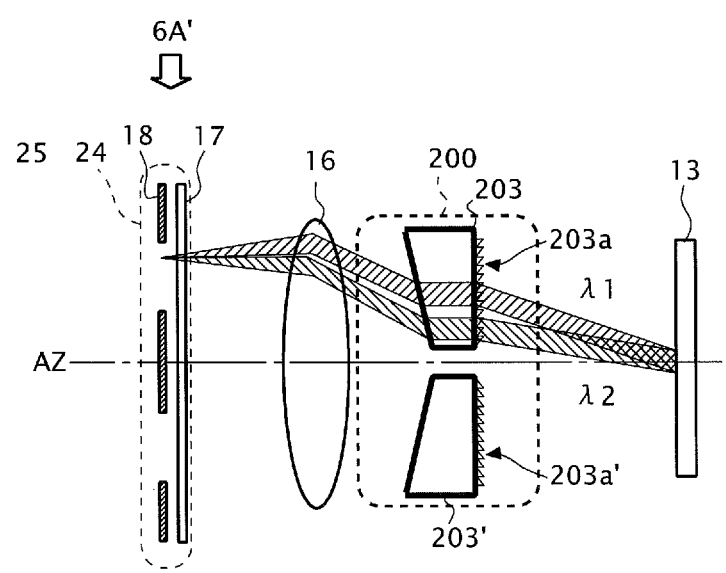
FIG. 20 is a diagram explaining a space adjusting part 200 of a fourth embodiment.

FIG. 20 is a diagram explaining a space adjusting part 200 of the fourth embodiment. Note that in FIG. 20, an illustration of the − first-order diffracted light flux is omitted, and the + first-order diffracted light flux with the long wavelength $\lambda 1$ and the + first-order diffracted light flux with the short wavelength $\lambda 2$ are illustrated at the same time. In FIG. 20, a light flux exited at a large diffraction angle from the diffraction grating 13 corresponds to the + first-order diffracted light flux with the long wavelength $\lambda 1$, and a light flux exited at a small diffraction angle from the diffraction grating 13 corresponds to the + first-order diffracted light flux with the short wavelength $\lambda 2$.

As illustrated in FIG. 20, the space adjusting part 200 of the present embodiment includes a pair of prisms 203 and 203' having shapes symmetric about the optical axis AZ and made of mutually the same material. A disposition place of the prism 203 being one of the pair of prisms is an optical path of the + first-order diffracted light flux, and a disposition place of the other prism 203' is an optical path of the − first-order diffracted light flux. A thickness in the optical axis AZ direction of each of the prisms 203 and 203' is set to be increased as a distance from the optical axis AZ increases. Further, as a material of each of the pair of prisms 203 and 203', a material in which a dispersion with respect to the wavelengths $\lambda 1$ and $\lambda 2$ is as low as possible, is employed.

Meanwhile, in the present embodiment, a diffractive optical surface 203a and a diffractive optical surface 203a' are individually formed on a light incident surface of the prism 203, and a light incident surface of the prism 203', respectively. A relationship between a structure of the diffractive optical surface 203a and a structure of the diffractive optical surface 203a' is symmetric about the optical axis AZ.

Each of the prisms 203 and 203' as above has both of a function as a prism and a function as a diffraction grating. Each of the prisms 203 and 203' as above can also be regarded as a "diffraction grating realized by forming a diffraction pattern on a wedge-shaped substrate".

The diffractive optical surfaces 203a and 203a' operate to set both of an angle of the wavelength $\lambda 1$ and an angle of the wavelength $\lambda 2$ in the prisms to have small values (zero, for example), by suppressing angles of the ± first-order diffracted light fluxes exited from the diffraction grating 13, particularly, by strongly suppressing the angle of the long wavelength $\lambda 1$.

For this reason, a structural pitch of each of the diffractive optical surfaces 203a and 203a' is set to be nearly equal to the structural pitch of the diffraction grating 13.

Note that although an illustration is omitted, at the diffractive optical surface 203a, diffracted components of respective orders with different angles are generated. However, in the present embodiment, an effective light ray exited from the diffractive optical surface 203a and capable of reaching the specimen 5 is assumed to be only a first-order diffracted component generated at the diffractive optical surface 203a, and an ineffective light ray generated at the diffractive optical surface 203a is ignored, as illustrated in FIG. 19.

In like manner, diffracted components of respective orders are generated also at the diffractive optical surface 203a'. However, in the present embodiment, an effective light ray exited from the diffractive optical surface 203a' and capable of reaching the specimen 5 is assumed to be only a + first-order diffracted component generated at the diffractive optical surface 203a', and an ineffective light ray generated at the diffractive optical surface 203a' is ignored.

Meanwhile, in the present embodiment, the structural pitch of each of the diffractive optical surfaces 203a and 203a' is set to be nearly equal to the structural pitch of the diffraction grating 13, as described above.

Therefore, each of the angle of the wavelength λ1 in the prism and the angle of the wavelength λ2 in the prism becomes approximately zero.

Note that the diffractive optical surfaces 203a and 203a' can be formed by previously preparing diffractive optical elements and attaching the diffractive optical elements to the light incident surface of the prism 203 and the light incident surface of the prism 203', or they can also be directly formed on the light incident surface of the prism 203 and the light incident surface of the prism 203', respectively, through etching or the like.

Further, as described above, the thickness in the optical axis AZ direction of each of the pair of prisms 203 and 203' is set to be increased as the distance from the optical axis AZ increases, and besides, the dispersion in the material of the pair of prisms 203 and 203' with respect to the wavelengths λ1 and λ2 is set to be as low as possible.

Therefore, the pair of light fluxes having the common wavelength (one of the light fluxes is not illustrated in FIG. 20) are deflected, when being exited from the prisms, in directions separating from each other, and besides, the deflection angles are approximately common between the wavelengths λ1 and λ2, as illustrated in FIG. 20.

Therefore, as illustrated in FIG. 20, angles of light rays directed to the collecting lens 16 become equal between the wavelengths λ1 and λ2, resulting in that heights of collecting points on the pupil conjugate plate 6A' (heights of collecting points on the pupil plane 6A) also become equal between the wavelengths λ1 and λ2.

Therefore, also in the present embodiment, it is possible to achieve an effect similar to that of the second embodiment.

Note that in the present embodiment, if the angles of light rays in the prisms are completely matched between the wavelengths λ1 and λ2, the angles of light rays that exit from the prisms are slightly deviated between the wavelengths λ1 and λ2. This is because it is not possible to set the dispersion of the prism to be completely zero.

Accordingly, in the present embodiment, it is desirable to set the structural pitch of each of the diffractive optical surfaces 203a and 203a' to be slightly greater than the structural pitch of the diffraction grating 13 so that angles of light rays right after being exited from the prisms are completely matched between the wavelengths λ1 and λ2.

Modified Example of Fourth Embodiment

Note that the fourth embodiment can also be modified in a similar manner to the second embodiment.

For example, the disposition place of the space adjusting part 200 in the fourth embodiment can be changed in a similar manner to that of the first embodiment.

For example, when the disposition place of the space adjusting part 200 in the fourth embodiment is set to a place where the + first-order diffracted light flux and the − first-order diffracted light flux propagate while approaching each other (a place between the lens 25 and the field stop 26), it is only required to invert the shape of each of the prisms 203 and 203'. Specifically, the thickness in the optical axis AZ direction of each of the pair of prisms 203 and 203' is set to be reduced as the distance from the optical axis AZ increases.

Further, in the space adjusting part 200 of the fourth embodiment, the place of formation of each of the diffractive optical surfaces 203a and 203a' is set to be the incident surface side of each of the prisms 203 and 203', but, it may also be set to an exit surface side of each of the prisms 203 and 203'.

Further, in the space adjusting part 200 of the fourth embodiment, the place of formation of the diffractive optical surface is set to the prism (wedge-shaped substrate), but, it may also be set to a parallel plate. Note that in that case, it is designed such that a combination of a posture of disposed parallel plate and the structural pitch of the diffractive optical surface is optimized to make angles of light rays (angles of light rays with the wavelengths λ1 and λ2) exited from the parallel plate have proper values other than zero.

Operation and Effect of Fourth Embodiment

As described above, an adjusting unit (200) of the fourth embodiment includes a diffractive optical surface (203a and 203a'), in which a structural pitch of the diffractive optical surface (203a and 203a') is set to be nearly equal to a structural pitch of the diffractive optical element (13) branching an exit light flux.

Further, the adjusting unit (200) of the fourth embodiment includes a refractive element (203 and 203') disposed at a place where two branched light fluxes propagate while separating from each other, in which the diffractive optical surface (203a and 203a') is formed on a surface of the refractive element (203 and 203'), and a thickness in an optical axis (AZ) direction of the refractive element (203 and 203') is set to be increased as a distance from the optical axis (AZ) increases.

Alternatively, the adjusting unit (not illustrated) of the fourth embodiment includes a refractive element (not illustrated) disposed at a place where two branched light fluxes propagate while approaching each other, and the diffractive optical element (not illustrated) formed on the refractive element (not illustrated), in which a thickness in an optical axis (AZ) direction of the refractive element (not illustrated) is set to be reduced as a distance from the optical axis (AZ) increases.

Therefore, the fourth embodiment can also achieve an effect similar to that of the second embodiment.

Fifth Embodiment

Hereinafter, a modified example of the first embodiment will be described as a fifth embodiment of the present invention. Here, only a point of difference between the present embodiment and the first embodiment will be described. The point of difference lies in a point that the illuminating optical system has a variable power function mounted thereon, instead of including the space adjusting part.

Figure 21A:
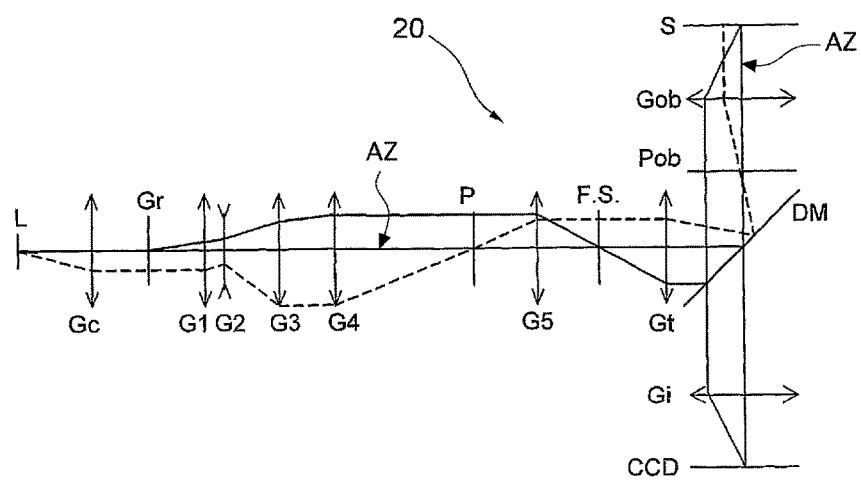
FIGS. 21A and 21B are schematic configuration diagrams of a structured illuminating microscopy in a fifth embodiment.
Figure 21B:
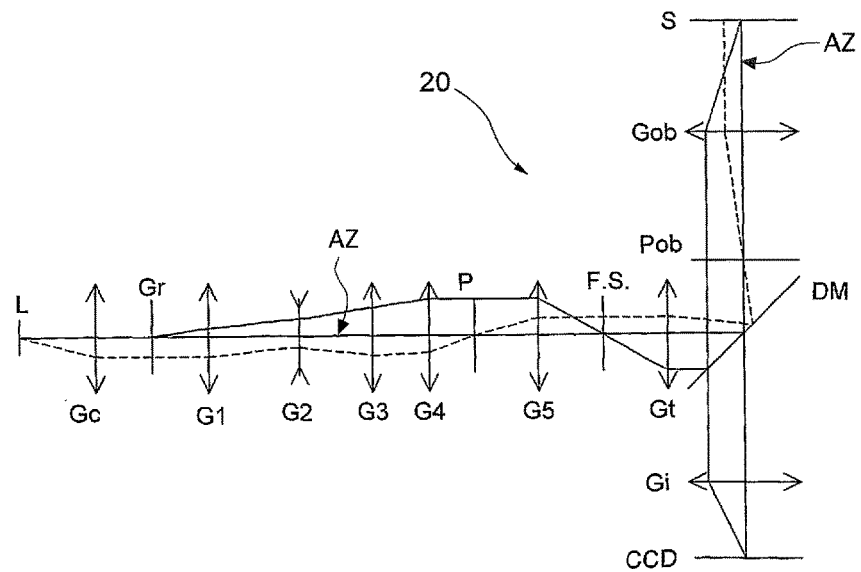

FIGS. 21A and 21B are schematic configuration diagrams of a structured illuminating microscopy in the present embodiment, in which FIG. 21A illustrates a state where a relay variable power optical system is in a high power end state, and FIG. 21B illustrates a state where the relay variable power optical system is in a low power end state.

In FIGS. 21A and 21B, an illustration of elements which are not necessary for the explanation such as, for example, a wavelength plate, a beam selecting element, a mechanism, and a controlling device, is omitted.

In FIGS. 21A and 21B, a symbol L denotes a point light source, a symbol Gc denotes a collector lens, a symbol Gr denotes a diffraction grating, a symbol P denotes a pupil conjugate plane, a symbol F.S. denotes a field stop, a symbol Gt denotes a field lens, a symbol DM denotes a dichroic mirror, a symbol Pob denotes a pupil of objective lens, a symbol Gob denotes an objective lens, a symbol S denotes a specimen plane, a symbol Gi denotes an image-forming lens (secondary objective lens), and a symbol CCD denotes an imaging plane. Further, a solid line in FIGS. 21A and 21B indicates a light ray related to a conjugation between the diffraction grating Gr and the specimen plane S, and a dotted line indicates a light ray related to a conjugation between the point light source L and the pupil Pob of the objective lens Gob.

In FIGS. 21A and 21B, a first lens group G1 to a fifth lens group G5 (a first lens group G1 having a positive refractive power, a second lens group G2 having a negative refractive power, a third lens group G3 having a positive refractive power, a fourth lens group G4 having a positive refractive power, and a fifth lens group G5 having a positive refractive power) configure the relay variable power optical system. Out of the above, the first lens group G1 to the fourth lens group G4 correspond to a variable power optical system having a variable power function, and the fifth lens group G5 corresponds to an image-forming optical system having an image-forming function. Note that a place where the diffraction grating Gr is disposed is at a position of front focal point of the relay variable power optical system formed of G1 to G5.

Meanwhile, as indicated by the dotted line in FIGS. 21A and 21B, the light ray from the light source L is turned into a collimated light by the collector lens Gc to illuminate the diffraction grating Gr. The light ray from the diffraction grating Gr is subjected to power variation by the variable power optical system (G1 to G4), and then an image of the light ray is formed at a position of the field stop F.S. by the image-forming optical system (G5). The light ray from the field stop F.S. is turned into a convergent light by the field lens Gt and reflected by the dichroic mirror DM, and after that, the light is collected at a position of the pupil Pob, and turned into a collimated light by the objective lens Gob to illuminate the specimen plane S.

Further, as indicated by the solid line in FIGS. 21A and 21B, the light ray from the specimen plane S is captured by the objective lens Gob, and after the light ray passes through the pupil Pob, it transmits through the dichroic mirror DM, and an image of the light ray is formed on the imaging plane CCD by the image-forming lens Gi.

In the structured illuminating microscopy apparatus of the present embodiment, when the light source wavelength is set to the long wavelength $\lambda 1$ (namely, when the diffraction angle of the ± first-order diffracted light fluxes at the diffraction grating Gr is large), a disposition place of each of the first lens group G1 to the fifth lens group G5 is set so that the power of the relay variable power optical system formed of G1 to G5 becomes low (refer to FIG. 21B), and when the light source wavelength is set to the short wavelength $\lambda 2$ (namely, when the diffraction angle of the ± first-order diffracted light fluxes at the diffraction grating Gr is small), the disposition place of each of the first lens group G1 to the fifth lens group G5 is set so that the power of the relay variable power optical system formed of G1 to G5 becomes high (refer to FIG. 21A), which enables the super-resolution effect to be common between the wavelengths $\lambda 1$ and $\lambda 2$.

Particularly, in the structured illuminating microscopy apparatus of the present embodiment, when the power of the relay variable power optical system formed of G1 to G5 (namely, the disposition place of each of the first lens group G1 to the fifth lens group G5) is controlled to make the collecting points of the ± first-order diffracted light fluxes to be positioned within the aforementioned TIRF area, it is also possible to maintain the generation condition of evanescent field (TIRF-condition).

Further, it is also possible to give a collecting position displacement characteristic depending on the wavelength, to the relay variable power optical system formed of G1 to G5. Concretely, the collecting position displacement characteristic corresponds to a collecting position displacement characteristic in a direction orthogonal to the optical axis AZ. Hereinafter, the collecting position displacement characteristic is simply referred to as "chromatic aberration of magnification".

The chromatic aberration of magnification is set so that the collecting points of the ± first-order diffracted light fluxes are kept positioned within the TIRF area regardless of the switching of the use wavelength $\lambda$.

The chromatic aberration of magnification $dY(\lambda)$ satisfies the following conditional expression.

$$(fo \cdot nw - af\lambda/P) \leq dY(\lambda) \leq (fo \cdot NA - af\lambda/P),$$

$$a=1 \text{ (when } M=1,2),$$

$$a=2 \text{ (when } M=3) \tag{2}$$

Note that M indicates a number of direction of structural pitch possessed by the diffraction grating Gr, $\lambda$ indicates each of a plurality of wavelengths, and $dY(\lambda)$ indicates a chromatic aberration of magnification of the relay variable power optical system formed of G1 to G5 when an image height is $2f \cdot \lambda_0/P$, in which a reference of the plurality of wavelengths is set to $\lambda_0$. Further, fo indicates a focal length of the objective lens Gob, f indicates a focal length of the relay variable power optical system formed of G1 to G5, P indicates a grating pitch of the diffraction grating Gr, NA indicates a numerical aperture of the objective lens Gob, and nw indicates a refractive index of the specimen.

Incidentally, since a cell is set to the specimen in the present embodiment, nw is nearly equal to a refractive index of water. Further, the number of direction of the pitch structure of the diffraction grating Gr is set to three in the present embodiment, so that M equals to three.

Hereinafter, a meaning of the conditional expression (2) will be described.

First, when the grating pitch of the diffraction grating Gr is P, and the number of direction of the pitch structure of the diffraction grating Gr is M, a diffraction angle $\theta$ of first-order diffracted lights generated at the diffraction grating Gr in accordance with a laser light with the use wavelength $\lambda$, is represented by the following expression.

Here, since $\theta$ is extremely small, an approximation that $\sin \theta = \theta$ is made.

$$\theta = a\lambda/P,$$

$$a=1 \text{ (when } M=1,2),$$

$$a=2 \text{ (when } M=3) \tag{3}$$

Further, if the relay variable power optical system formed of G1 to G5 is tentatively stigmatic one, and if the focal length of the relay variable power optical system formed of G1 to G5 is f, each of the first-order diffracted lights exited from the diffraction grating Gr at the diffraction angle $\theta$ is collected at a position, on the pupil plane, at which a height from the optical axis AZ is Y. The height Y can be represented by the following expression.

Here, since θ is extremely small, an approximation that tan θ=θ is made.

$$Y = f\theta \quad (4)$$

Further, when the focal length of the objective lens Gob is fo, and the numerical aperture of the objective lens Gob is NA, a pupil radius r of the objective lens Gob is represented by the following expression.

$$r = foNA \quad (5)$$

Therefore, if $(Y+dY(\lambda))$ satisfies the following conditional expression without depending on the switching of the use wavelength λ, the collecting points of the first-order diffracted lights are kept positioned within the TIRF area without depending on the switching of the use wavelength λ. Specifically, the TIRF-condition is maintained.

$$nwfo \leq Y + dY(\lambda) \leq r \quad (6)$$

If the expressions (3), (4), and (5) are substituted in the expression (6), and the expression is solved for dY, the conditional expression (2) is obtained.

As a result of the above, it can be understood that the conditional expression (2) corresponds to a conditional expression for making the collecting points of the ± first-order diffracted lights to be kept positioned within the TIRF area (for maintaining the TIRF-condition) without depending on the switching of the use wavelength λ.

Further, in a structured illuminating microscopy apparatus of the present embodiment, an optical system (the relay variable power optical system formed of G1 to G5) which is rotationally symmetric about an optical axis (AZ), is used for controlling a height from the optical axis (AZ) to each of collecting points, so that a symmetry of the respective collecting points about the optical axis (AZ) is securely maintained.

Further, in a structured illuminating microscopy apparatus of the present embodiment, an optical system (the relay variable power optical system formed of G1 to G5) which is rotationally symmetric about an optical axis (AZ), is used for controlling a height from the optical axis (AZ) to each of collecting points, so that it is also possible to deal with the switching of direction of an interference fringe.

Further, in the structured illuminating microscopy apparatus of the present embodiment, even if a power of the relay variable power optical system formed of G1 to G5 is varied, a position of exit pupil of the relay variable power optical system formed of G1 to G5 is not varied almost at all, so that a telecentricity of the structured illuminating microscopy apparatus is maintained.

Further, in the present embodiment, the pupil of the variable power optical system formed of G1 to G4 is positioned on the outside of the variable power optical system formed of G1 to G4 (behind the variable power optical system), so that even if an optical element which controls the interference fringe (the aforementioned beam selecting part or the like) is disposed on the pupil, the optical element does not hinder a power variation performed by the relay variable power optical system formed of G1 to G5.

Modified Example of Fifth Embodiment

Note that there is no problem even if at least one lens group in the fifth embodiment is formed of a plurality of lenses or a single lens. Further, there is no problem even if the single lens is a cemented lens formed by cementing a plurality of lenses.

Further, the fifth embodiment can also be modified in a similar manner to the first embodiment.

For example, in the fifth embodiment, the number of switching of the light source wavelength may also be increased to three or more. In that case, it is only required to set a number of variable step of the power of the relay variable power optical system formed of G1 to G5 (the disposition place of each of the lens groups G1 to G5) to three or more.

Further, in the fifth embodiment, it is also possible to set such that the power of the relay variable power optical system formed of G1 to G5 (the disposition place of each of the first lens group G1 to the fifth lens group G5) is variable in a period of time during which the light source wavelength is fixed.

Note that even in that case, it is desirable to limit an adjustment range of the power of the relay variable power optical system formed of G1 to G5 (the disposition place of each of the first lens group G1 to the fifth lens group G5) to keep the collecting points of the ± first-order diffracted light fluxes to be placed within the aforementioned TIRF area.

If it is designed as above, it is possible to perform fine adjustment of a depth of the evanescent field (=a leakage amount of evanescent light with respect to the specimen 5) while maintaining the generation condition of the evanescent field (TIRF-condition).

Further, the controlling device 39 desirably performs the fine adjustment in accordance with an instruction from a user. Accordingly, it becomes possible for the user to freely adjust the depth of the evanescent field.

Operation and Effect of Fifth Embodiment

As described above, an adjusting unit (G1 to G5) of the fifth embodiment corresponds to a variable power optical system formed of a plurality of lens groups, in which a disposition of the plurality of lens groups is set in accordance with a wavelength of the two branched light fluxes, namely, a deflection angle given to the two branched light fluxes by the branching unit (Gr).

Therefore, in the fifth embodiment, it is possible to achieve an effect similar to that of the first embodiment.

[Others]

Note that the illuminating optical system 10 of each of the first embodiment to the fifth embodiment is configured by the epi-illuminating optical system formed of the objective lens 6, but, the configuration is not limited to this, and it is also possible to configure the illuminating optical system 10 using transmission/reflection illuminating optical system formed of a condenser lens, instead of the objective lens 6. In that case, a place at which collecting points are formed is a pupil plane of the condenser lens.

Further, the requirements of the above-described respective embodiments can be appropriately combined. Further, there is a case where a part of the components is not used. Further, disclosures of all laid-open application publications and U.S. patents related to the apparatus and the like cited in the above-described respective embodiments and modified examples are incorporated by reference as a part of this specification, as long as allowed by law.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A structured illuminating apparatus, comprising:
a brancher that branches an exit light flux from a light source into at least two branched light fluxes;
an illuminating optical system that (i) directs two of the branched light fluxes to a first position on a pupil plane of an objective lens and a second position on the pupil plane, respectively, and (ii) generates an interference fringe on a specimen by the two of the branched light fluxes;
an image-forming optical system that forms an image on a light detector by an observational light flux from the specimen modulated by the interference fringe;
a calculator that calculates a demodulated image of the specimen based on an image generated by the light detector; and
an adjuster that adjusts (i) a distance from the first position on the pupil plane to an optical axis of the objective lens and (ii) a distance from the second position on the pupil plane to the optical axis to adjust a resolution of the demodulated image or to satisfy a generation condition of an evanescent field.

2. The structured illuminating apparatus according to claim 1, wherein
the adjuster includes an optical element that deflects the two of the branched light fluxes at a deflection angle in accordance with a wavelength of the two of the branched light fluxes.

3. The structured illuminating apparatus according to claim 1, wherein:
the adjuster includes:
a first reflecting surface that deflects an optical path of a first light flux of the two of the branched light fluxes;
a second reflecting surface that returns a direction of the optical path of the first light flux deflected by the first reflecting surface to an original direction;
a third reflecting surface that deflects an optical path of a second light flux of the two of the branched light fluxes; and
a fourth reflecting surface that returns a direction of the optical path of the second light flux deflected by the third reflecting surface to an original direction, and
at least one of a positional relationship between the first reflecting surface and the third reflecting surface and a positional relationship between the second reflecting surface and the fourth reflecting surface is variable.

4. The structured illuminating apparatus according to claim 1, wherein:
the adjuster is a variable power optical system formed of a plurality of lens groups, and
a disposition of the plurality of lens groups is set in accordance with a deflection angle given to the two of the branched light fluxes by the brancher.

5. The structured illuminating apparatus according to claim 1, further comprising: an optical fiber that guides the exit light from the light source, wherein a position of an exit end of the optical fiber is changeable in an optical axis direction.

6. The structured illuminating apparatus according to claim 1, wherein the adjuster keeps a positional relationship between the first position and the second position to a relationship symmetric about the optical axis.

7. The structured illuminating apparatus according to claim 1, wherein the brancher is a diffractive optical element.

8. The structured illuminating apparatus according to claim 1, wherein:
the light source can switch a wavelength of the exit light flux; and
each of the distances is adjusted to have a predetermined value regardless of the switching of the wavelength.

9. The structured illuminating apparatus according to claim 1, further comprising a switcher that switches the first position and the second position among a plurality of rotating positions around the optical axis, wherein the adjuster is provided for each of the plurality of rotating positions.

10. The structured illuminating apparatus according to claim 1, further comprising:
a first switcher that switches the first position and the second position among a plurality of rotating positions around the optical axis; and
a second switcher that switches a position of the adjuster among the plurality of rotating positions.

11. The structured illuminating apparatus according to claim 1, further comprising a phase shifter that shifts a phase of the interference fringe.

12. The structured illuminating apparatus according to claim 1, wherein each of the distances is adjusted to a value within a predetermined range.

13. The structured illuminating apparatus according to claim 12, wherein the predetermined range is a range in which the two of the branched light fluxes can generate the evanescent field in a vicinity of a surface of the specimen.

14. The structured illuminating apparatus according to claim 12, wherein each of the distances is finely adjusted within the predetermined range in accordance with an instruction from a user.

15. The structured illuminating apparatus according to claim 1, wherein:
the brancher is a diffractive optical element; and
the adjuster respectively sets, between an exit light flux of a first wavelength and an exit light flux of a second wavelength, the distance from the first position to the optical axis of the objective lens and the distance from the second position to the optical axis approximately the same.

16. The structured illuminating apparatus according to claim 15, wherein:
the adjuster is formed of an element deflecting each of the two of the branched light fluxes; and
a difference of a deflection angle between the exit light flux of the first wavelength and the exit light flux of the second wavelength set by the adjuster is a value canceling a difference of a diffraction angle between the exit light flux of the first wavelength and the exit light flux of the second wavelength.

17. The structured illuminating apparatus according to claim 15, wherein the light source makes the exit light fluxes of the first and second wavelengths exit simultaneously or sequentially.

18. The structured illuminating apparatus according to claim 15, further comprising: a switcher that switches the first position and the second position among a plurality of rotating positions around the optical axis, wherein the adjuster is provided for each of the plurality of rotating positions.

19. The structured illuminating apparatus according to claim 15, further comprising:

a first switcher that switches the first position and the second position among a plurality of rotating positions around the optical axis; and a second switcher that switches a position of the adjuster among the plurality of rotating positions.

20. The structured illuminating apparatus according to claim 15, further comprising a phase shifter that shifts a phase of the interference fringe.

21. The structured illuminating apparatus according to claim 15, wherein a disposition place of the adjuster is a place where the two of the branched light fluxes are spatially separated.

22. The structured illuminating apparatus according to claim 21, wherein:

the adjuster includes a refractive element disposed at a place where the two of the branched light fluxes propagate while approaching each other, and a thickness in an optical axis direction of the refractive element is reduced as a distance from the optical axis increases.

23. The structured illuminating apparatus according to claim 21, wherein:

the adjuster includes a diffractive optical surface, and a structural pitch of the diffractive optical surface is nearly equal to a structural pitch of the diffractive optical element branching the exit light flux.

24. The structured illuminating apparatus according to claim 23, wherein:

the adjuster includes a refractive element disposed at a place where the two of the branched light fluxes propagate while separating from each other, and the diffractive optical surface is formed on a surface of the refractive element and a thickness in an optical axis direction of the refractive element is increased as a distance from the optical axis increases.

25. The structured illuminating apparatus according to claim 23, wherein:

the adjuster includes a refractive element disposed at a place where the two of the branched light fluxes propagate while approaching each other, and the diffractive optical surface is formed on a surface of the refractive element and a thickness in an optical axis direction of the refractive element is reduced as a distance from the optical axis increases.

26. The structured illuminating apparatus according to claim 21, wherein:

the adjuster includes a refractive element disposed at a place where the two of the branched light fluxes propagate while separating from each other, and a thickness in an optical axis direction of the refractive element is increased as a distance from the optical axis increases.

27. The structured illuminating apparatus according to claim 26, wherein:

the adjuster further includes a supplementary refractive element disposed in front of or behind the refractive element and having a dispersion weaker than a dispersion of the refractive element, and a thickness in the optical axis direction of the supplementary refractive element is reduced as a distance from the optical axis increases.

28. The structured illuminating apparatus according to claim 22, wherein:

the adjuster further includes a supplementary refractive element disposed in front of or behind the refractive element and having a dispersion weaker than a dispersion of the refractive element, and a thickness in the optical axis direction of the supplementary refractive element is increased as a distance from the optical axis increases.

* * * * *